(12) United States Patent
Koerber et al.

(10) Patent No.: US 8,563,474 B2
(45) Date of Patent: Oct. 22, 2013

(54) PESTCIDAL ACTIVE MIXTURES COMPRISING ISOXAZOLINE COMPOUNDS I

(75) Inventors: Karsten Koerber, Eppelheim (DE); Florian Kaiser, Mannheim (DE); Juergen Langewald, Mannheim (DE)

(73) Assignee: BASF SE, Ludwigshafen (DE)

( * ) Notice: Subject to any disclaimer, the term of this patent is extended or adjusted under 35 U.S.C. 154(b) by 23 days.

(21) Appl. No.: 13/003,037

(22) PCT Filed: Jul. 6, 2009

(86) PCT No.: PCT/EP2009/058517
§ 371 (c)(1),
(2), (4) Date: Jan. 7, 2011

(87) PCT Pub. No.: WO2010/003923
PCT Pub. Date: Jan. 14, 2010

(65) Prior Publication Data
US 2011/0118212 A1    May 19, 2011

Related U.S. Application Data

(60) Provisional application No. 61/079,318, filed on Jul. 9, 2008.

(51) Int. Cl.
*A01N 43/80* (2006.01)
*A01N 43/56* (2006.01)
*A01P 7/04* (2006.01)

(52) U.S. Cl.
USPC ........... 504/138; 504/140; 504/149; 504/139; 548/240; 548/377.1; 548/373.1; 564/180; 564/182

(58) Field of Classification Search
USPC .................. 504/138, 140, 149, 139; 548/240, 548/377.1, 373.1; 564/182
See application file for complete search history.

(56) References Cited

U.S. PATENT DOCUMENTS

| | | | |
|---|---|---|---|
| 3,917,698 | A | 11/1975 | Breslow |
| 6,313,344 | B1 | 11/2001 | Trah et al. |
| 6,521,643 | B1 | 2/2003 | Tomishima et al. |
| 2003/0119806 | A1 | 6/2003 | Lindell et al. |
| 2004/0014801 | A1 | 1/2004 | Cohen et al. |
| 2007/0066617 | A1 | 3/2007 | Mita et al. |
| 2009/0023923 | A1 | 1/2009 | Mizukoshi et al. |
| 2009/0156643 | A1 | 6/2009 | Mita et al. |
| 2010/0144797 | A1 | 6/2010 | Mita et al. |
| 2010/0144808 | A1 | 6/2010 | Mita et al. |
| 2010/0160683 | A1 | 6/2010 | Matoba et al. |
| 2010/0286175 | A1 | 11/2010 | Grammenos et al. |
| 2011/0172414 | A1 | 7/2011 | Mita et al. |

FOREIGN PATENT DOCUMENTS

| | | |
|---|---|---|
| CA | 2 547 744 | 12/2006 |
| CH | 577487 | 7/1976 |
| CH | 595365 | 2/1978 |
| CH | 608011 | 12/1978 |
| CN | 1 927 860 | 3/2007 |
| DE | 10 2004 010 086 | 9/2004 |
| EP | 0 539 676 | 5/1993 |
| EP | 1 538 138 | 6/2005 |
| EP | 1 731 512 | 12/2006 |
| EP | 1932836 | 6/2008 |
| EP | 1 997 813 | 12/2008 |
| EP | 2 151 437 | 2/2010 |
| EP | 2 186 804 | 5/2010 |

(Continued)

OTHER PUBLICATIONS

International Search Report for International Application No. PCT/EP2009/058517.

(Continued)

*Primary Examiner* — Sreeni Padmanabhan
*Assistant Examiner* — Irina Neagu
(74) *Attorney, Agent, or Firm* — Brinks, Hofer, Gilson & Lione

(57) ABSTRACT

The present invention relates to pesticidal mixtures comprising as active compounds
1) at least one isoaxazoline compound I of the formula (I)

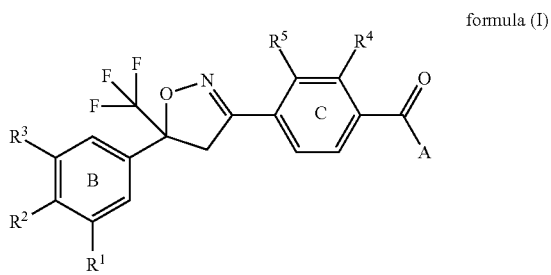

formula (I)

wherein $R^1$, $R^2$, $R^3$, $R^4$, $R^5$ and A are defined in the description;
and
2) at least one active compound II selected from a group A comprising acteylcholine esterase inhibitors, GABA-gated chloride channel antagonists, sodium channel modulators, nicotinic acteylcholine receptor agonists/antagonists, chloride channel activators, juvenile hormone mimics, compounds affecting the oxidative phosphorylation, inhibitors of the chitin biosynthesis, moulting disruptors, inhibitors of the MET, voltage-dependent sodium channel blockers, inhibitors of the lipid synthesis and other compounds as defined in the description, in synergistically effective amounts.
The invention relates further to methods and use of these mixtures for combating insects, arachnids or nematodes in and on plants, and for protecting such plants being infested with pests, especially also for protecting plant propagation material as like seeds.

17 Claims, No Drawings

(56) References Cited

FOREIGN PATENT DOCUMENTS

| | | |
|---|---|---|
| EP | 2199287 | 6/2010 |
| JP | 2007 016017 | 1/2007 |
| JP | 2007 106756 | 4/2007 |
| JP | 2007 308471 | 11/2007 |
| JP | 2008 239611 | 10/2008 |
| JP | 2009 108046 | 5/2009 |
| WO | WO 01/17964 | 3/2001 |
| WO | WO 02/068392 | 9/2002 |
| WO | WO 03/022808 | 3/2003 |
| WO | WO 03/062222 | 7/2003 |
| WO | WO 03/067987 | 8/2003 |
| WO | WO 2004/018410 | 3/2004 |
| WO | WO 2004/060371 | 7/2004 |
| WO | WO 2004/060865 | 7/2004 |
| WO | WO 2005/036961 | 4/2005 |
| WO | WO 2005/085216 | 9/2005 |
| WO | WO 2006/010570 | 2/2006 |
| WO | WO 2006/021833 | 3/2006 |
| WO | WO 2006/065659 | 6/2006 |
| WO | WO 2007/026965 | 3/2007 |
| WO | WO 2007/070606 | 6/2007 |
| WO | WO 2007/074789 | 7/2007 |
| WO | WO 2007/075459 | 7/2007 |
| WO | WO2007/079162 * | 7/2007 |
| WO | WO 2007/081019 | 7/2007 |
| WO | WO 2007/093599 | 8/2007 |
| WO | WO 2007/094313 | 8/2007 |
| WO | WO 2007/105814 | 9/2007 |
| WO | WO 2007/125984 | 11/2007 |
| WO | WO 2008/012027 | 1/2008 |
| WO | WO 2008/019760 | 2/2008 |
| WO | WO 2008/022937 | 2/2008 |
| WO | WO 2008/070831 | 6/2008 |
| WO | WO 2008/108448 | 9/2008 |
| WO | WO 2008/122375 | 10/2008 |
| WO | WO 2008/126665 | 10/2008 |
| WO | WO 2008/130651 | 10/2008 |
| WO | WO 09/002809 * | 12/2008 |
| WO | WO 2008/154528 | 12/2008 |
| WO | WO 2009/005015 | 1/2009 |
| WO | WO 2009/022746 | 2/2009 |
| WO | WO 2009/025983 | 2/2009 |
| WO | WO 2009/035004 | 3/2009 |
| WO | WO 2009/045999 | 4/2009 |
| WO | WO 2009/049846 | 4/2009 |
| WO | WO 2009/077197 | 6/2009 |
| WO | WO 2009/112275 | 9/2009 |
| WO | WO 2009/126668 | 10/2009 |
| WO | WO 2010/003877 | 1/2010 |
| WO | WO 2010/020521 | 2/2010 |
| WO | WO 2010/020522 | 2/2010 |
| WO | WO 2010/072602 | 7/2010 |
| WO | WO 2010/072781 | 7/2010 |
| WO | WO 2010/112545 | 10/2010 |
| WO | WO 2011/073444 | 2/2011 |

OTHER PUBLICATIONS

International Preliminary Report on Patentability for International Application No. PCT/EP2009/058517.

Belen'Kii et al, Database: Beilstein, XP002580907 database accession No. 1988095, Russian Chem. Bull., (1997), pp. 101-104, vol. 46, No. 1.

"DMP 754 Roxifiban Acetate", Drugs of the Future, (1998), pp. 707-711, vol. 23(7).

Hosking, M., et al., "Roxifiban DuPont", Current Opinion in Cardiovascular, Pulmonary & Renal Investigational Drugs, (2000), pp. 165-171, vol. 2(2).

Kaugars, G. et al., "Miticidal activity of benzoyl chloride phenylhydrazones", Journal of Agriculture and Food Chem., (1973), pp. 647-650, vol. 21, No. 4.

Kiriyama, K. et al., "Insecticidal and Neuroblocking Activities of Acetamiprid and Related Compounds", Journal of Pesticide Science, (2003), pp. 8-17, vol. 28.

Wierenga, J. et al., "Insecticidal activity of N-arylalkylbenzhydrolpiperidines", Pest Management Science, (2002), pp. 1266-1272, vol. 58.

Walters, Matthew J. et al., "The preparation of 5-Aryl-5-methyl-4,5-dihydroisoxazoles from dilithiated C($\alpha$), O-oximes and Select Acetyl Ketones", Synthetic Communications, 2003, p. 4163-4171, vol. 33, No. 23.

Office Action dated Oct. 24, 2012, from U.S. Appl. No. 13/003,032.
Office Action dated Jan. 29, 2013, from U.S. Appl. No. 13/141,264.

* cited by examiner

PESTCIDAL ACTIVE MIXTURES COMPRISING ISOXAZOLINE COMPOUNDS I

This application is a National Stage application of International Application No. PCT/EP2009/058517 filed Jul. 6, 2009, which claims the benefit of U.S. Provisional Application No. 61/079,318, filed Jul. 9, 2008, the entire contents of which are hereby incorporated herein by reference.

The present invention relates to mixtures of active ingredients having synergistically enhanced action and to methods comprising applying said mixtures.

One typical problem arising in the field of pest control lies in the need to reduce the dosage rates of the active ingredient in order to reduce or avoid unfavorable environmental or toxicological effects whilst still allowing effective pest control.

Another problem encountered concerns the need to have available pest control agents which are effective against a broad spectrum of pests.

There also exists the need for pest control agents that combine know-down activity with prolonged control, that is, fast action with long lasting action.

Another difficulty in relation to the use of pesticides is that the repeated and exclusive application of an individual pesticidal compound leads in many cases to a rapid selection of pests which have developed natural or adapted resistance against the active compound in question. Therefore there is a need for pest control agents that help prevent or overcome resistance.

It was therefore an object of the present invention to provide pesticidal mixtures which solves at least one of the discussed problems as reducing the dosage rate, enhancing the spectrum of activity or combining know-down activity with prolonged control or as to resistance management.

We have found that this object is in part or in whole achieved by the combination of active compounds defined below.

The present invention relates to pesticidal mixtures comprising as active compounds
1) at least one isoxazoline compound I of formula I:

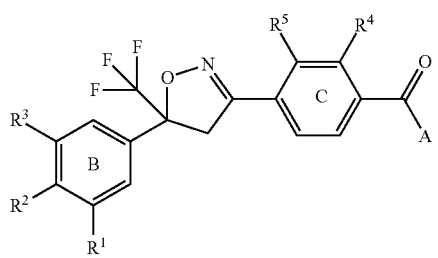

formula (I)

wherein
A is selected from

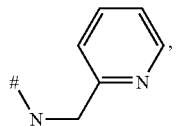

A-1

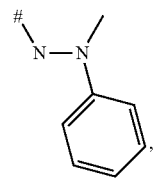

A-2

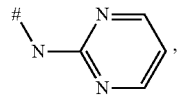

A-3

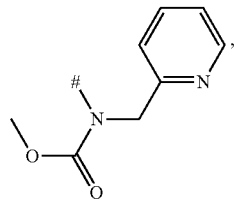

A-4

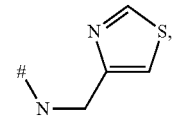

A-5

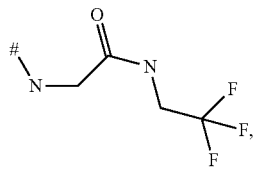

A-6

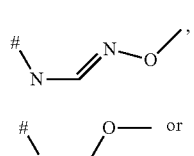

A-7

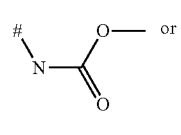

A-8

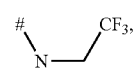

A-9 and wherein # denotes the bond in formula I;
$R^1$, $R^3$ are independently from one another selected from hydrogen, chloro or $CF_3$;
$R^2$ is hydrogen or chloro;
$R^4$ is hydrogen or $CH_3$,
$R^5$ is hydrogen, or
$R^4$ and $R^5$ are together a bridging 1,3-butadienyl group, which form—together with the aromatic phenylring C they are attached to—a naphtyl ring;
or the tautomers, enantiomers, diastereomers or salts thereof, and
2) at least one active compound II selected from group A consisting of
A.1 Acetylcholine esterase inhibitors selected from triazemate or from the class of carbamates consisting of aldicarb, alanycarb, benfuracarb, carbaryl, carbofuran, carbosulfan, methiocarb, methomyl, oxamyl, primicarb, propoxur and thiodicarb or from the class of organophosphates consisting of acephate, azinphos-ethyl, azinphos-methyl, chlorfenvinphos, chlorpyrifos, chlorpyrifos-methyl, demeton-S-methyl, diazinon, dichlorvos/DDVP, dicrotophos, dimethoate, disulfoton, ethion, fenitrothion, fenthion, isoxathion, malathion, methamidaphos, methidathion, mevinphos, monocrotophos, oxymethoate, oxydemeton-methyl, parathion, parathion-methyl, phenthoate, phorate, phosalone, phosmet, phosphamidon, pirimiphos-methyl, quinalphos, terbufos, tetrachlorvinphos, triazophos and trichlorfon;

A.2 GABA-gated chloride channel antagonists selected from the cyclodiene organochlorine endosulfan, from N-Ethyl-2, 2-dimethylpropionamide-2-(2,6-dichloro-α.α.α-trifluoro-p-tolyl)hydrazon or N-Ethyl-2,2-dichloro-1-methylcyclopropane-carboxamide-2-(2,6-dichloro-α.α.α-trifluoro-p-tolyl)hydrazon or from the class of phenylpyrazoles consisting of acetoprole, ethiprole, fipronil, pyrafluprole, pyriprole, vaniliprole and the phenylpyrazole compound II.A$^{2.1}$:

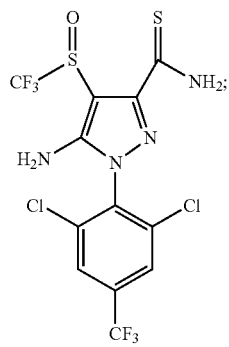

(II.A$^{2.1}$)

A.3 Sodium channel modulators selected from the class of pyrethroids consisting of allethrin, bifenthrin, beta-cyfluthrin, cyfluthrin, lambda-cyhalothrin, cypermethrin, alpha-cypermethrin, beta-cypermethrin, zeta-cypermethrin, deltamethrin, esfenvalerate, etofenprox, fenpropathrin, fenvalerate, flucythrinate, metofluthrin, permethrin, profluthrin, pyrethrin (pyrethrum), tau-fluvalinate, silafluofen and tralomethrin;

A.4 Nicotinic aceylcholine receptor agonists/antagonists selected from nicotin, cartap hydrochloride or thiocyclam or selected from the class of neonicotinoids consisting of acetamiprid, chlothianidin, dinotefuran, imidacloprid, nitenpyram, spinosad (allosteric agonist), spinetroam (allosteric agonist), thiacloprid, thiamethoxam and AKD-1022;

A.5 Chloride channel activators selected from abamectin, emamectin benzoate, lepimectin or milbemectin;

A.6 Juvenile hormone mimics selected from hydroprene, kinoprene, fenoxycarb or pyriproxyfen;

A.7 Compounds affecting the oxidative phosphorylation selected from diafenthiuron, fenbutatin oxide, propargite or chlorfenapyr;

A.8 Inhibitors of the chitin biosynthesis selected from buprofezin or from the class of benzylureas consisting of bistrifluoron, diflubenzuron, flufenoxuron, hexaflumuron, lufenuron, novaluron or teflubenzuron;

A.9 Moulting disruptors selected from cyromazine or from the class of ecdysone agonists consisting of methoxyfenozide, tebufenozide and azadirachtin;

A.10 Mitochondrial electron transport inhibitors selected from pyridaben, tolfenpyrad or flufenerim.

A.11 Voltage-dependent sodium channel blockers selected from indoxacarb or metaflumizone.

A.12 Inhibitors of the lipid synthesis selected from spirodiclofen, spiromesifen or spirotetramat.

A.13 A group of various compounds consisting of amidoflumet, amitraz, bifenazate, clofentezine, cyenopyrafen, cyflumetofen, etoxazole, flonicamid, flubendiamine, flupyrazophos, hexythiazox, piperonyl butoxide, pymetrozine, pyridalyl, pyrifluquinazon, chlorantraniliprole and the anthranilamid compound II.A$^{13.1}$:

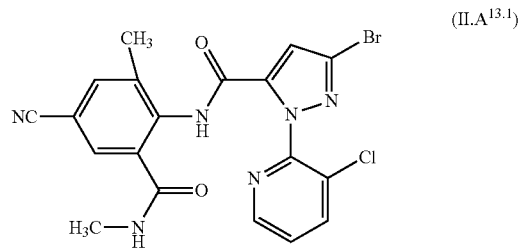 [SMILES: CNC(=O)c1cc(C#N)cc(C)c1NC(=O)c1cc(Br)nn1-c1ncccc1Cl]

(II.A$^{13.1}$)

and the anthranilamid compounds
5-Bromo-2-(3-chloro-pyridin-2-yl)-2H-pyrazole-3-carboxylic acid[4-cyano-2-(1-cyclopropyl-ethylcarbamoyl)-6-methyl-phenyl]-amide,
5-Bromo-2-(3-chloro-pyridin-2-yl)-2H-pyrazole-3-carboxylic acid[2-chloro-4-cyano-6-(1-cyclopropyl-ethylcarbamoyl)-phenyl]-amide,
5-Bromo-2-(3-chloro-pyridin-2-yl)-2H-pyrazole-3-carboxylic acid[2-bromo-4-cyano-6-(1-cyclopropyl-ethylcarbamoyl)-phenyl]-amide,
5-Bromo-2-(3-chloro-pyridin-2-yl)-2H-pyrazole-3-carboxylic acid[2-bromo-4-chloro-6-(1-cyclopropyl-ethylcarbamoyl)-phenyl]-amide,
5-Bromo-2-(3-chloro-pyridin-2-yl)-2H-pyrazole-3-carboxylic acid[2,4-dichloro-6-(1-cyclopropyl-ethylcarbamoyl)-phenyl]-amide,
5-Bromo-2-(3-chloro-pyridin-2-yl)-2H-pyrazole-3-carboxylic acid[4-chloro-2-(1-cyclopropyl-ethylcarbamoyl)-6-methyl-phenyl]-amide,
N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester,
N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester,
N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester,
N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester,
N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester and
N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester,
the aminofuranone compounds
4-{[(6-Bromopyrid-3-yl)methyl](2-fluoroethyl)amino}furan-2(5H)-on,
4-{[(6-Fluoropyrid-3-yl)methyl](2,2-difluoroethyl)amino}furan-2(5H)-on,
4-{[(2-Chloro 1,3-thiazolo-5-yl)methyl](2-fluoroethyl)amino}furan-2(5H)-on,
4-{[(6-Chloropyrid-3-yl)methyl](2-fluoroethyl)amino}furan-2(5H)-on,
4-{[(6-Chloropyrid-3-yl)methyl](2,2-difluoroethyl)amino}furan-2(5H)-on, 4-{[(6-Chloro-5-fluoropyrid-3-yl)methyl](methyl)amino}furan-2(5H)-on, 4-{[(5,6-Dichloropyrid-3-yl)methyl](2-fluoroethyl)amino}furan-2(5H)-on, 4-{[(6-Chloro-5-fluoropyrid-3-yl)methyl](cyclopropyl)amino}furan-2(5H)-on, 4-{[(6-Chloropyrid-3-yl)methyl](cyclopropyl)amino}furan-2(5H)-on and 4-{[(6-Chloropyrid-3-yl)methyl](methyl)amino}furan-2(5H)-on, the malononitrile compounds 2-(2,2,3,3,4,4,5,5-octafluoropentyl)-2-(3,3,3-trifluoropropyl)malononitrile ($CF_2H$—$CF_2$—$CF_2$—$CF_2$—$CH_2$—$C(CN)_2$—$CH_2$—$CH_2$—$CF_3$) and 2-(2,2,3,3,4,4,5,5-octafluoropentyl)-2-(3,3,4,4,4-pentafluorobutyl)-malonodinitrile ($CF_2H$—$CF_2$—$CF_2$—$CF_2$—$CH_2$—$C(CN)_2$—$CH_2$—$CH_2$—$CF_2$—$CF_3$), the alkynylether compound 4-But-2-ynyloxy-6-(3,5-dimethyl-piperidin-1-yl)-2-fluoro-pyrimidine, the sulfoximine compounds $IIA^{13.2}$

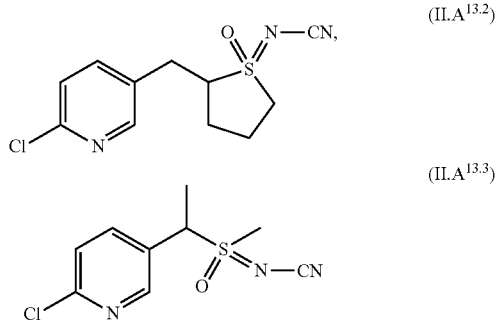

and $II.A^{13.4}$

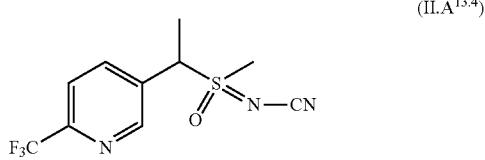 [SMILES: CC(c1ccc(C(F)(F)F)nc1)S(C)(=O)=NC#N]

the phtalamid compound (R)—, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid ($II.A^{13.5}$), the pyripyropene compound Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester ($II.A^{13.6}$) and the pyridazine compound 8-(2-Cyclopropylmethoxy-4-trifluoromethyl-phenoxy)-3-(6-trifluoromethyl-pyridazin-3-yl)-3-aza-bicyclo[3.2.1]octane ($II.A^{13.7}$)

in synergistically effective amounts.

Moreover, we have found that simultaneous, that is joint or separate, application of one or more active compound I and one or more compounds II or successive application of one or more active compound I and one or more active compounds II allows enhanced control of pests compared to the control rates that are possible with the individual compounds.

The present invention also provides methods for the control of insects, acarids or nematodes comprising contacting the insect, acarid or nematode or their food supply, habitat, breeding grounds or their locus with a pesticidally effective amount of mixtures of at least one active compound I with at least one active compound II.

Moreover, the present invention also relates to a method of protecting plants from attack or infestation by insects, acarids or nematodes comprising contacting the plant, or the soil or water in which the plant is growing, with a pesticidally effective amount of a mixture of at least one active compound I with at least one active compound II.

The invention also provides a method for the protection of seeds from soil insects and of the seedlings' roots and shoots from soil and foliar insects which comprises contacting the seeds before sowing and/or after pregermination with a pesticidally effective amount of a mixture of at least one active compound I with at least one active compound II.

The invention also provides seeds comprising a mixture of at least one active compound I with at least one active compound II.

The invention also relates to the use of a mixture of at least one active compound I with at least one active compound II for combating insects, arachnids or nematodes.

The invention also provides the use of a mixture of at least one active compound I with at least one active compound II for combating parasites in and on animals.

The invention provides further a method for treating, controlling, preventing or protecting animals against infestation or infection by parasites which comprises orally, topically or parenterally administering or applying to the animals a parasiticidally effective amount of a mixture of at least one active compound I with at least one active compound II.

Another aspect of the present invention is a process for the preparation of a composition for treating, controlling, preventing or protecting animals against infestation or infection by parasites which comprises a parasiticidally effective amount of a mixture of the active compound I with at least one active compound II.

Pesticidal active isoxazoline compounds have been described in WO05/085219, WO2007/075459, WO2008/019760 and WO2008/012027. Further isoxazoline compounds comprising annelated bicyclic moieties, as an naphtyl group, are disclosed in WO2007/079162. Preparation methods are described in WO 2007/074789 and WO 2007/094313. In general, pesticidal active isoxazoline compounds are also described in JP 2007/016017, JP 2007/106756, WO 2005/085216, WO 2007/026965, WO 2007/105814, WO 2007/125984 WO 2007/026965, JP 2008-239611, WO 2008108448, WO 2009/005015, WO 2009/035004, WO 2008/150393, WO 2008/154528, WO 2009/002809, WO 2009/003075, WO 2009/025983, WO 2009/051956, WO 2009/022746, WO 2009/049846, WO 2008/126665, US 2008/00262057 and WO 2009/024541.

The prior art does not disclose pesticidal mixtures comprising selective isoxazoline compounds according to the present invention showing unexpected and synergistic effects in combination with other pesticidally active compounds.

The commercially available compounds of the group A may be found in The Pesticide Manual, 13$^{th}$ Edition, British Crop Protection Council (2003) among other publications. Thiamides derivatives in analogy of formula $II.A^{2.1}$ and their preparation have been described in WO 98/28279. Lepimectin is known from Agro Project, PJB Publications Ltd, November 2004. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP-A 2002-193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP-A 21010907. Flufenerim and its preparation have been described in WO 03/007717 and in WO 03/007718. Cyflumetofen and its preparation have been described in WO 04/080180. Preparation methods for neonicotionids similar to AKD-1022 have been described by Zhang, A. et al. in J. Neurochemistry, 75(3), 2000. Anthranilamides like chloranthraniliprole and derivatives in analogy of formula II.A$^{13.1}$ and their preparation have been described in WO 01/70671; WO 02/48137; WO 03/24222, WO 03/15518, WO 03/15519, WO 04/67528; WO 04/33468 and WO 05/118552. Further anthranilamides have also been described in WO 2008/72743, WO 200872783 and WO 2007/043677. Malononitrile compounds have been described e.g. in WO 02/089579, WO 02/090320, WO 02/090321, WO 04/006677, WO 05/068423, WO 05/068432 and WO 05/063694. The alkynylether compound is described e.g. in JP 2006131529. Sulfoximine derivatives of and in analogy of formulae II.A$^{13.2}$, II.A$^{13.3}$ or II.A$^{13.4}$ and their preparations have been described in WO 2006/060029. The phthalamide compound (II.A$^{13.5}$) is known from WO 2007/101540 The aminofuranone compounds have been described e.g. in WO 2007/115644. The pyripyropene derivative (II.A$^{13.6}$) has been described in WO 2008/66153 and WO 2008/108491. The pyridazin compound (II.A$^{13.7}$) has been described in JP 2008/115155.

Preferences
Preferred Compounds I of Formula I
With regard to their use in the pesticidal mixtures of the present invention, compounds I of formula I are preferred, wherein
A is A-1, A-4 or A-6;
$R^1$, $R^3$ are independently from one another selected from hydrogen, chloro or $CF_3$;
$R^2$ is hydrogen or chloro;
$R^4$ is hydrogen oder $CH_3$,
$R^5$ is hydrogen or
$R^4$ and $R^5$ are together a bridging 1,3-butadienyl group, which form—together with the aromatic phenylring C they are attached to—a naphtyl ring;
Especially preferred are compounds I of formula I having the following meanings:
A is A-1, A-4 or A-6;
$R^1$, $R^2$, $R^3$ are chloro;
$R^4$ is hydrogen oder $CH_3$,
$R^5$ is hydrogen or
$R^4$ and $R^5$ are together a bridging 1,3-butadienyl group, which form—together with the aromatic phenylring C they are attached to—a naphtyl ring;
Especially preferred are compounds I of formula I having the following meanings:
A is A-1, A-4 or A-6;
$R^1$, $R^3$ are chloro;
$R^2$ is hydrogen;
$R^4$ is hydrogen oder $CH_3$,
$R^5$ is hydrogen or
$R^4$ and $R^5$ are together a bridging 1,3-butadienyl group, which form—together with the aromatic phenylring C they are attached to—a naphtyl ring;
Further preferred are compounds I of formula I having the following meanings:
A is A-1, A-4 or A-6;
$R^1$, $R^3$ are $CF_3$;
$R^2$ is hydrogen;
$R^4$ is hydrogen oder $CH_3$,
$R^5$ is hydrogen or
$R^4$ and $R^5$ are together a bridging 1,3-butadienyl group, which form—together with the aromatic phenylring C they are attached to—a naphtyl ring;
or
A is A-1, A-4 or A-6;
$R^1$ is $CF_3$;
$R^2$, $R^3$ are hydrogen;
$R^4$ is hydrogen oder $CH_3$,
$R^5$ is hydrogen or
$R^4$ and $R^5$ are together a bridging 1,3-butadienyl group, which form—together with the aromatic phenylring C they are attached to—a naphtyl ring;
Compound I examples of isoxazoline compounds of formula I are given in the following table C.I.1:

TABLE C.I.1

| Compound I | A | $R^1$ | $R^2$ | $R^3$ | $R^4$ | $R^5$ |
|---|---|---|---|---|---|---|
| C.I-1 | A-1 | H | H | H | H | H |
| C.I-2 | A-2 | H | H | H | H | H |
| C.I-3 | A-3 | H | H | H | H | H |
| C.I-4 | A-4 | H | H | H | H | H |
| C.I-5 | A-5 | H | H | H | H | H |
| C.I-6 | A-6 | H | H | H | H | H |
| C.I-7 | A-7 | H | H | H | H | H |
| C.I-8 | A-8 | H | H | H | H | H |
| C.I-9 | A-9 | H | H | H | H | H |
| C.I-10 | A-1 | H | Cl | H | H | H |
| C.I-11 | A-2 | H | Cl | H | H | H |
| C.I-12 | A-3 | H | Cl | H | H | H |
| C.I-13 | A-4 | H | Cl | H | H | H |
| C.I-14 | A-5 | H | Cl | H | H | H |
| C.I-15 | A-6 | H | Cl | H | H | H |
| C.I-16 | A-7 | H | Cl | H | H | H |
| C.I-17 | A-8 | H | Cl | H | H | H |
| C.I-18 | A-9 | H | Cl | H | H | H |
| C.I-19 | A-1 | Cl | H | H | H | H |
| C.I-20 | A-2 | Cl | H | H | H | H |
| C.I-21 | A-3 | Cl | H | H | H | H |
| C.I-22 | A-4 | Cl | H | H | H | H |
| C.I-23 | A-5 | Cl | H | H | H | H |
| C.I-24 | A-6 | Cl | H | H | H | H |
| C.I-25 | A-7 | Cl | H | H | H | H |
| C.I-26 | A-8 | Cl | H | H | H | H |
| C.I-27 | A-9 | Cl | H | H | H | H |
| C.I-28 | A-1 | Cl | Cl | H | H | H |
| C.I-29 | A-2 | Cl | Cl | H | H | H |
| C.I-30 | A-3 | Cl | Cl | H | H | H |
| C.I-31 | A-4 | Cl | Cl | H | H | H |
| C.I-32 | A-5 | Cl | Cl | H | H | H |
| C.I-33 | A-6 | Cl | Cl | H | H | H |
| C.I-34 | A-7 | Cl | Cl | H | H | H |
| C.I-35 | A-8 | Cl | Cl | H | H | H |
| C.I-36 | A-9 | Cl | Cl | H | H | H |
| C.I-37 | A-1 | $CF_3$ | H | H | H | H |
| C.I-38 | A-2 | $CF_3$ | H | H | H | H |
| C.I-39 | A-3 | $CF_3$ | H | H | H | H |
| C.I-40 | A-4 | $CF_3$ | H | H | H | H |
| C.I-41 | A-5 | $CF_3$ | H | H | H | H |
| C.I-42 | A-6 | $CF_3$ | H | H | H | H |
| C.I-43 | A-7 | $CF_3$ | H | H | H | H |
| C.I-44 | A-8 | $CF_3$ | H | H | H | H |
| C.I-45 | A-9 | $CF_3$ | H | H | H | H |
| C.I-46 | A-1 | $CF_3$ | Cl | H | H | H |
| C.I-47 | A-2 | $CF_3$ | Cl | H | H | H |
| C.I-48 | A-3 | $CF_3$ | Cl | H | H | H |
| C.I-49 | A-4 | $CF_3$ | Cl | H | H | H |
| C.I-50 | A-5 | $CF_3$ | Cl | H | H | H |
| C.I-51 | A-6 | $CF_3$ | Cl | H | H | H |
| C.I-52 | A-7 | $CF_3$ | Cl | H | H | H |
| C.I-53 | A-8 | $CF_3$ | Cl | H | H | H |
| C.I-54 | A-9 | $CF_3$ | Cl | H | H | H |
| C.I-55 | A-1 | H | H | Cl | H | H |
| C.I-56 | A-2 | H | H | Cl | H | H |
| C.I-57 | A-3 | H | H | Cl | H | H |

TABLE C.I.1-continued

| Compound I | A | R¹ | R² | R³ | R⁴ | R⁵ |
|---|---|---|---|---|---|---|
| C.I-58 | A-4 | H | H | Cl | H | H |
| C.I-59 | A-5 | H | H | Cl | H | H |
| C.I-60 | A-6 | H | H | Cl | H | H |
| C.I-61 | A-7 | H | H | Cl | H | H |
| C.I-62 | A-8 | H | H | Cl | H | H |
| C.I-63 | A-9 | H | H | Cl | H | H |
| C.I-64 | A-1 | H | Cl | Cl | H | H |
| C.I-65 | A-2 | H | Cl | Cl | H | H |
| C.I-66 | A-3 | H | Cl | Cl | H | H |
| C.I-67 | A-4 | H | Cl | Cl | H | H |
| C.I-68 | A-5 | H | Cl | Cl | H | H |
| C.I-69 | A-6 | H | Cl | Cl | H | H |
| C.I-70 | A-7 | H | Cl | Cl | H | H |
| C.I-71 | A-8 | H | Cl | Cl | H | H |
| C.I-72 | A-9 | H | Cl | Cl | H | H |
| C.I-73 | A-1 | Cl | H | Cl | H | H |
| C.I-74 | A-2 | Cl | H | Cl | H | H |
| C.I-75 | A-3 | Cl | H | Cl | H | H |
| C.I-76 | A-4 | Cl | H | Cl | H | H |
| C.I-77 | A-5 | Cl | H | Cl | H | H |
| C.I-78 | A-6 | Cl | H | Cl | H | H |
| C.I-79 | A-7 | Cl | H | Cl | H | H |
| C.I-80 | A-8 | Cl | H | Cl | H | H |
| C.I-81 | A-9 | Cl | H | Cl | H | H |
| C.I-82 | A-1 | Cl | Cl | Cl | H | H |
| C.I-83 | A-2 | Cl | Cl | Cl | H | H |
| C.I-84 | A-3 | Cl | Cl | Cl | H | H |
| C.I-85 | A-4 | Cl | Cl | Cl | H | H |
| C.I-86 | A-5 | Cl | Cl | Cl | H | H |
| C.I-87 | A-6 | Cl | Cl | Cl | H | H |
| C.I-88 | A-7 | Cl | Cl | Cl | H | H |
| C.I-89 | A-8 | Cl | Cl | Cl | H | H |
| C.I-90 | A-9 | Cl | Cl | Cl | H | H |
| C.I-91 | A-1 | $CF_3$ | H | Cl | H | H |
| C.I-92 | A-2 | $CF_3$ | H | Cl | H | H |
| C.I-93 | A-3 | $CF_3$ | H | Cl | H | H |
| C.I-94 | A-4 | $CF_3$ | H | Cl | H | H |
| C.I-95 | A-5 | $CF_3$ | H | Cl | H | H |
| C.I-96 | A-6 | $CF_3$ | H | Cl | H | H |
| C.I-97 | A-7 | $CF_3$ | H | Cl | H | H |
| C.I-98 | A-8 | $CF_3$ | H | Cl | H | H |
| C.I-99 | A-9 | $CF_3$ | H | Cl | H | H |
| C.I-100 | A-1 | $CF_3$ | Cl | Cl | H | H |
| C.I-101 | A-2 | $CF_3$ | Cl | Cl | H | H |
| C.I-102 | A-3 | $CF_3$ | Cl | Cl | H | H |
| C.I-103 | A-4 | $CF_3$ | Cl | Cl | H | H |
| C.I-104 | A-5 | $CF_3$ | Cl | Cl | H | H |
| C.I-105 | A-6 | $CF_3$ | Cl | Cl | H | H |
| C.I-106 | A-7 | $CF_3$ | Cl | Cl | H | H |
| C.I-107 | A-8 | $CF_3$ | Cl | Cl | H | H |
| C.I-108 | A-9 | $CF_3$ | Cl | Cl | H | H |
| C.I-109 | A-1 | H | H | $CF_3$ | H | H |
| C.I-110 | A-2 | H | H | $CF_3$ | H | H |
| C.I-111 | A-3 | H | H | $CF_3$ | H | H |
| C.I-112 | A-4 | H | H | $CF_3$ | H | H |
| C.I-113 | A-5 | H | H | $CF_3$ | H | H |
| C.I-114 | A-6 | H | H | $CF_3$ | H | H |
| C.I-115 | A-7 | H | H | $CF_3$ | H | H |
| C.I-116 | A-8 | H | H | $CF_3$ | H | H |
| C.I-117 | A-9 | H | H | $CF_3$ | H | H |
| C.I-118 | A-1 | H | Cl | $CF_3$ | H | H |
| C.I-119 | A-2 | H | Cl | $CF_3$ | H | H |
| C.I-120 | A-3 | H | Cl | $CF_3$ | H | H |
| C.I-121 | A-4 | H | Cl | $CF_3$ | H | H |
| C.I-122 | A-5 | H | Cl | $CF_3$ | H | H |
| C.I-123 | A-6 | H | Cl | $CF_3$ | H | H |
| C.I-124 | A-7 | H | Cl | $CF_3$ | H | H |
| C.I-125 | A-8 | H | Cl | $CF_3$ | H | H |
| C.I-126 | A-9 | H | Cl | $CF_3$ | H | H |
| C.I-127 | A-1 | Cl | H | $CF_3$ | H | H |
| C.I-128 | A-2 | Cl | H | $CF_3$ | H | H |
| C.I-129 | A-3 | Cl | H | $CF_3$ | H | H |
| C.I-130 | A-4 | Cl | H | $CF_3$ | H | H |
| C.I-131 | A-5 | Cl | H | $CF_3$ | H | H |
| C.I-132 | A-6 | Cl | H | $CF_3$ | H | H |
| C.I-133 | A-7 | Cl | H | $CF_3$ | H | H |
| C.I-134 | A-8 | Cl | H | $CF_3$ | H | H |
| C.I-135 | A-9 | Cl | H | $CF_3$ | H | H |
| C.I-136 | A-1 | Cl | Cl | $CF_3$ | H | H |
| C.I-137 | A-2 | Cl | Cl | $CF_3$ | H | H |
| C.I-138 | A-3 | Cl | Cl | $CF_3$ | H | H |
| C.I-139 | A-4 | Cl | Cl | $CF_3$ | H | H |
| C.I-140 | A-5 | Cl | Cl | $CF_3$ | H | H |
| C.I-141 | A-6 | Cl | Cl | $CF_3$ | H | H |
| C.I-142 | A-7 | Cl | Cl | $CF_3$ | H | H |
| C.I-143 | A-8 | Cl | Cl | $CF_3$ | H | H |
| C.I-144 | A-9 | Cl | Cl | $CF_3$ | H | H |
| C.I-145 | A-1 | $CF_3$ | H | $CF_3$ | H | H |
| C.I-146 | A-2 | $CF_3$ | H | $CF_3$ | H | H |
| C.I-147 | A-3 | $CF_3$ | H | $CF_3$ | H | H |
| C.I-148 | A-4 | $CF_3$ | H | $CF_3$ | H | H |
| C.I-149 | A-5 | $CF_3$ | H | $CF_3$ | H | H |
| C.I-150 | A-6 | $CF_3$ | H | $CF_3$ | H | H |
| C.I-151 | A-7 | $CF_3$ | H | $CF_3$ | H | H |
| C.I-152 | A-8 | $CF_3$ | H | $CF_3$ | H | H |
| C.I-153 | A-9 | $CF_3$ | H | $CF_3$ | H | H |
| C.I-154 | A-1 | $CF_3$ | Cl | $CF_3$ | H | H |
| C.I-155 | A-2 | $CF_3$ | Cl | $CF_3$ | H | H |
| C.I-156 | A-3 | $CF_3$ | Cl | $CF_3$ | H | H |
| C.I-157 | A-4 | $CF_3$ | Cl | $CF_3$ | H | H |
| C.I-158 | A-5 | $CF_3$ | Cl | $CF_3$ | H | H |
| C.I-159 | A-6 | $CF_3$ | Cl | $CF_3$ | H | H |
| C.I-160 | A-7 | $CF_3$ | Cl | $CF_3$ | H | H |
| C.I-161 | A-8 | $CF_3$ | Cl | $CF_3$ | H | H |
| C.I-162 | A-9 | $CF_3$ | Cl | $CF_3$ | H | H |
| C.I-163 | A-1 | H | H | H | $CH_3$ | H |
| C.I-164 | A-2 | H | H | H | $CH_3$ | H |
| C.I-165 | A-3 | H | H | H | $CH_3$ | H |
| C.I-166 | A-4 | H | H | H | $CH_3$ | H |
| C.I-167 | A-5 | H | H | H | $CH_3$ | H |
| C.I-168 | A-6 | H | H | H | $CH_3$ | H |
| C.I-169 | A-7 | H | H | H | $CH_3$ | H |
| C.I-170 | A-8 | H | H | H | $CH_3$ | H |
| C.I-171 | A-9 | H | H | H | $CH_3$ | H |
| C.I-172 | A-1 | H | Cl | H | $CH_3$ | H |
| C.I-173 | A-2 | H | Cl | H | $CH_3$ | H |
| C.I-174 | A-3 | H | Cl | H | $CH_3$ | H |
| C.I-175 | A-4 | H | Cl | H | $CH_3$ | H |
| C.I-176 | A-5 | H | Cl | H | $CH_3$ | H |
| C.I-177 | A-6 | H | Cl | H | $CH_3$ | H |
| C.I-178 | A-7 | H | Cl | H | $CH_3$ | H |
| C.I-179 | A-8 | H | Cl | H | $CH_3$ | H |
| C.I-180 | A-9 | H | Cl | H | $CH_3$ | H |
| C.I-181 | A-1 | Cl | H | H | $CH_3$ | H |
| C.I-182 | A-2 | Cl | H | H | $CH_3$ | H |
| C.I-183 | A-3 | Cl | H | H | $CH_3$ | H |
| C.I-184 | A-4 | Cl | H | H | $CH_3$ | H |
| C.I-185 | A-5 | Cl | H | H | $CH_3$ | H |
| C.I-186 | A-6 | Cl | H | H | $CH_3$ | H |
| C.I-187 | A-7 | Cl | H | H | $CH_3$ | H |
| C.I-188 | A-8 | Cl | H | H | $CH_3$ | H |
| C.I-189 | A-9 | Cl | H | H | $CH_3$ | H |
| C.I-190 | A-1 | Cl | Cl | H | $CH_3$ | H |
| C.I-191 | A-2 | Cl | Cl | H | $CH_3$ | H |
| C.I-192 | A-3 | Cl | Cl | H | $CH_3$ | H |
| C.I-193 | A-4 | Cl | Cl | H | $CH_3$ | H |
| C.I-194 | A-5 | Cl | Cl | H | $CH_3$ | H |
| C.I-195 | A-6 | Cl | Cl | H | $CH_3$ | H |
| C.I-196 | A-7 | Cl | Cl | H | $CH_3$ | H |
| C.I-197 | A-8 | Cl | Cl | H | $CH_3$ | H |
| C.I-198 | A-9 | Cl | Cl | H | $CH_3$ | H |
| C.I-199 | A-1 | $CF_3$ | H | H | $CH_3$ | H |
| C.I-200 | A-2 | $CF_3$ | H | H | $CH_3$ | H |
| C.I-201 | A-3 | $CF_3$ | H | H | $CH_3$ | H |
| C.I-202 | A-4 | $CF_3$ | H | H | $CH_3$ | H |
| C.I-203 | A-5 | $CF_3$ | H | H | $CH_3$ | H |
| C.I-204 | A-6 | $CF_3$ | H | H | $CH_3$ | H |
| C.I-205 | A-7 | $CF_3$ | H | H | $CH_3$ | H |
| C.I-206 | A-8 | $CF_3$ | H | H | $CH_3$ | H |
| C.I-207 | A-9 | $CF_3$ | H | H | $CH_3$ | H |
| C.I-208 | A-1 | $CF_3$ | Cl | H | $CH_3$ | H |
| C.I-209 | A-2 | $CF_3$ | Cl | H | $CH_3$ | H |
| C.I-210 | A-3 | $CF_3$ | Cl | H | $CH_3$ | H |
| C.I-211 | A-4 | $CF_3$ | Cl | H | $CH_3$ | H |
| C.I-212 | A-5 | $CF_3$ | Cl | H | $CH_3$ | H |
| C.I-213 | A-6 | $CF_3$ | Cl | H | $CH_3$ | H |

TABLE C.I.1-continued

| Compound I | A | R¹ | R² | R³ | R⁴ | R⁵ |
|---|---|---|---|---|---|---|
| C.I-214 | A-7 | CF₃ | Cl | H | CH₃ | H |
| C.I-215 | A-8 | CF₃ | Cl | H | CH₃ | H |
| C.I-216 | A-9 | CF₃ | Cl | H | CH₃ | H |
| C.I-217 | A-1 | H | H | Cl | CH₃ | H |
| C.I-218 | A-2 | H | H | Cl | CH₃ | H |
| C.I-219 | A-3 | H | H | Cl | CH₃ | H |
| C.I-220 | A-4 | H | H | Cl | CH₃ | H |
| C.I-221 | A-5 | H | H | Cl | CH₃ | H |
| C.I-222 | A-6 | H | H | Cl | CH₃ | H |
| C.I-223 | A-7 | H | H | Cl | CH₃ | H |
| C.I-224 | A-8 | H | H | Cl | CH₃ | H |
| C.I-225 | A-9 | H | H | Cl | CH₃ | H |
| C.I-226 | A-1 | H | Cl | Cl | CH₃ | H |
| C.I-227 | A-2 | H | Cl | Cl | CH₃ | H |
| C.I-228 | A-3 | H | Cl | Cl | CH₃ | H |
| C.I-229 | A-4 | H | Cl | Cl | CH₃ | H |
| C.I-230 | A-5 | H | Cl | Cl | CH₃ | H |
| C.I-231 | A-6 | H | Cl | Cl | CH₃ | H |
| C.I-232 | A-7 | H | Cl | Cl | CH₃ | H |
| C.I-233 | A-8 | H | Cl | Cl | CH₃ | H |
| C.I-234 | A-9 | H | Cl | Cl | CH₃ | H |
| C.I-235 | A-1 | Cl | H | Cl | CH₃ | H |
| C.I-236 | A-2 | Cl | H | Cl | CH₃ | H |
| C.I-237 | A-3 | Cl | H | Cl | CH₃ | H |
| C.I-238 | A-4 | Cl | H | Cl | CH₃ | H |
| C.I-239 | A-5 | Cl | H | Cl | CH₃ | H |
| C.I-240 | A-6 | Cl | H | Cl | CH₃ | H |
| C.I-241 | A-7 | Cl | H | Cl | CH₃ | H |
| C.I-242 | A-8 | Cl | H | Cl | CH₃ | H |
| C.I-243 | A-9 | Cl | H | Cl | CH₃ | H |
| C.I-244 | A-1 | Cl | Cl | Cl | CH₃ | H |
| C.I-245 | A-2 | Cl | Cl | Cl | CH₃ | H |
| C.I-246 | A-3 | Cl | Cl | Cl | CH₃ | H |
| C.I-247 | A-4 | Cl | Cl | Cl | CH₃ | H |
| C.I-248 | A-5 | Cl | Cl | Cl | CH₃ | H |
| C.I-249 | A-6 | Cl | Cl | Cl | CH₃ | H |
| C.I-250 | A-7 | Cl | Cl | Cl | CH₃ | H |
| C.I-251 | A-8 | Cl | Cl | Cl | CH₃ | H |
| C.I-252 | A-9 | Cl | Cl | Cl | CH₃ | H |
| C.I-253 | A-1 | CF₃ | H | Cl | CH₃ | H |
| C.I-254 | A-2 | CF₃ | H | Cl | CH₃ | H |
| C.I-255 | A-3 | CF₃ | H | Cl | CH₃ | H |
| C.I-256 | A-4 | CF₃ | H | Cl | CH₃ | H |
| C.I-257 | A-5 | CF₃ | H | Cl | CH₃ | H |
| C.I-258 | A-6 | CF₃ | H | Cl | CH₃ | H |
| C.I-259 | A-7 | CF₃ | H | Cl | CH₃ | H |
| C.I-260 | A-8 | CF₃ | H | Cl | CH₃ | H |
| C.I-261 | A-9 | CF₃ | H | Cl | CH₃ | H |
| C.I-262 | A-1 | CF₃ | Cl | Cl | CH₃ | H |
| C.I-263 | A-2 | CF₃ | Cl | Cl | CH₃ | H |
| C.I-264 | A-3 | CF₃ | Cl | Cl | CH₃ | H |
| C.I-265 | A-4 | CF₃ | Cl | Cl | CH₃ | H |
| C.I-266 | A-5 | CF₃ | Cl | Cl | CH₃ | H |
| C.I-267 | A-6 | CF₃ | Cl | Cl | CH₃ | H |
| C.I-268 | A-7 | CF₃ | Cl | Cl | CH₃ | H |
| C.I-269 | A-8 | CF₃ | Cl | Cl | CH₃ | H |
| C.I-270 | A-9 | CF₃ | Cl | Cl | CH₃ | H |
| C.I-271 | A-1 | H | H | CF₃ | CH₃ | H |
| C.I-272 | A-2 | H | H | CF₃ | CH₃ | H |
| C.I-273 | A-3 | H | H | CF₃ | CH₃ | H |
| C.I-274 | A-4 | H | H | CF₃ | CH₃ | H |
| C.I-275 | A-5 | H | H | CF₃ | CH₃ | H |
| C.I-276 | A-6 | H | H | CF₃ | CH₃ | H |
| C.I-277 | A-7 | H | H | CF₃ | CH₃ | H |
| C.I-278 | A-8 | H | H | CF₃ | CH₃ | H |
| C.I-279 | A-9 | H | H | CF₃ | CH₃ | H |
| C.I-280 | A-1 | H | Cl | CF₃ | CH₃ | H |
| C.I-281 | A-2 | H | Cl | CF₃ | CH₃ | H |
| C.I-282 | A-3 | H | Cl | CF₃ | CH₃ | H |
| C.I-283 | A-4 | H | Cl | CF₃ | CH₃ | H |
| C.I-284 | A-5 | H | Cl | CF₃ | CH₃ | H |
| C.I-285 | A-6 | H | Cl | CF₃ | CH₃ | H |
| C.I-286 | A-7 | H | Cl | CF₃ | CH₃ | H |
| C.I-287 | A-8 | H | Cl | CF₃ | CH₃ | H |
| C.I-288 | A-9 | H | Cl | CF₃ | CH₃ | H |
| C.I-289 | A-1 | Cl | H | CF₃ | CH₃ | H |
| C.I-290 | A-2 | Cl | H | CF₃ | CH₃ | H |
| C.I-291 | A-3 | Cl | H | CF₃ | CH₃ | H |
| C.I-292 | A-4 | Cl | H | CF₃ | CH₃ | H |
| C.I-293 | A-5 | Cl | H | CF₃ | CH₃ | H |
| C.I-294 | A-6 | Cl | H | CF₃ | CH₃ | H |
| C.I-295 | A-7 | Cl | H | CF₃ | CH₃ | H |
| C.I-296 | A-8 | Cl | H | CF₃ | CH₃ | H |
| C.I-297 | A-9 | Cl | H | CF₃ | CH₃ | H |
| C.I-298 | A-1 | Cl | Cl | CF₃ | CH₃ | H |
| C.I-299 | A-2 | Cl | Cl | CF₃ | CH₃ | H |
| C.I-300 | A-3 | Cl | Cl | CF₃ | CH₃ | H |
| C.I-301 | A-4 | Cl | Cl | CF₃ | CH₃ | H |
| C.I-302 | A-5 | Cl | Cl | CF₃ | CH₃ | H |
| C.I-303 | A-6 | Cl | Cl | CF₃ | CH₃ | H |
| C.I-304 | A-7 | Cl | Cl | CF₃ | CH₃ | H |
| C.I-305 | A-8 | Cl | Cl | CF₃ | CH₃ | H |
| C.I-306 | A-9 | Cl | Cl | CF₃ | CH₃ | H |
| C.I-307 | A-1 | CF₃ | H | CF₃ | CH₃ | H |
| C.I-308 | A-2 | CF₃ | H | CF₃ | CH₃ | H |
| C.I-309 | A-3 | CF₃ | H | CF₃ | CH₃ | H |
| C.I-310 | A-4 | CF₃ | H | CF₃ | CH₃ | H |
| C.I-311 | A-5 | CF₃ | H | CF₃ | CH₃ | H |
| C.I-312 | A-6 | CF₃ | H | CF₃ | CH₃ | H |
| C.I-313 | A-7 | CF₃ | H | CF₃ | CH₃ | H |
| C.I-314 | A-8 | CF₃ | H | CF₃ | CH₃ | H |
| C.I-315 | A-9 | CF₃ | H | CF₃ | CH₃ | H |
| C.I-316 | A-1 | CF₃ | Cl | CF₃ | CH₃ | H |
| C.I-317 | A-2 | CF₃ | Cl | CF₃ | CH₃ | H |
| C.I-318 | A-3 | CF₃ | Cl | CF₃ | CH₃ | H |
| C.I-319 | A-4 | CF₃ | Cl | CF₃ | CH₃ | H |
| C.I-320 | A-5 | CF₃ | Cl | CF₃ | CH₃ | H |
| C.I-321 | A-6 | CF₃ | Cl | CF₃ | CH₃ | H |
| C.I-322 | A-7 | CF₃ | Cl | CF₃ | CH₃ | H |
| C.I-323 | A-8 | CF₃ | Cl | CF₃ | CH₃ | H |
| C.I-324 | A-9 | CF₃ | Cl | CF₃ | CH₃ | H |
| C.I-325 | A-1 | H | H | H | CH=CH—CH=CH | |
| C.I-326 | A-2 | H | H | H | CH=CH—CH=CH | |
| C.I-327 | A-3 | H | H | H | CH=CH—CH=CH | |
| C.I-328 | A-4 | H | H | H | CH=CH—CH=CH | |
| C.I-329 | A-5 | H | H | H | CH=CH—CH=CH | |
| C.I-330 | A-6 | H | H | H | CH=CH—CH=CH | |
| C.I-331 | A-7 | H | H | H | CH=CH—CH=CH | |
| C.I-332 | A-8 | H | H | H | CH=CH—CH=CH | |
| C.I-333 | A-9 | H | H | H | CH=CH—CH=CH | |
| C.I-334 | A-1 | H | Cl | H | CH=CH—CH=CH | |
| C.I-335 | A-2 | H | Cl | H | CH=CH—CH=CH | |
| C.I-336 | A-3 | H | Cl | H | CH=CH—CH=CH | |
| C.I-337 | A-4 | H | Cl | H | CH=CH—CH=CH | |
| C.I-338 | A-5 | H | Cl | H | CH=CH—CH=CH | |
| C.I-339 | A-6 | H | Cl | H | CH=CH—CH=CH | |
| C.I-340 | A-7 | H | Cl | H | CH=CH—CH=CH | |
| C.I-341 | A-8 | H | Cl | H | CH=CH—CH=CH | |
| C.I-342 | A-9 | H | Cl | H | CH=CH—CH=CH | |
| C.I-343 | A-1 | Cl | H | H | CH=CH—CH=CH | |
| C.I-344 | A-2 | Cl | H | H | CH=CH—CH=CH | |
| C.I-345 | A-3 | Cl | H | H | CH=CH—CH=CH | |
| C.I-346 | A-4 | Cl | H | H | CH=CH—CH=CH | |
| C.I-347 | A-5 | Cl | H | H | CH=CH—CH=CH | |
| C.I-348 | A-6 | Cl | H | H | CH=CH—CH=CH | |
| C.I-349 | A-7 | Cl | H | H | CH=CH—CH=CH | |
| C.I-350 | A-8 | Cl | H | H | CH=CH—CH=CH | |
| C.I-351 | A-9 | Cl | H | H | CH=CH—CH=CH | |
| C.I-352 | A-1 | Cl | Cl | H | CH=CH—CH=CH | |
| C.I-353 | A-2 | Cl | Cl | H | CH=CH—CH=CH | |
| C.I-354 | A-3 | Cl | Cl | H | CH=CH—CH=CH | |
| C.I-355 | A-4 | Cl | Cl | H | CH=CH—CH=CH | |
| C.I-356 | A-5 | Cl | Cl | H | CH=CH—CH=CH | |
| C.I-357 | A-6 | Cl | Cl | H | CH=CH—CH=CH | |
| C.I-358 | A-7 | Cl | Cl | H | CH=CH—CH=CH | |
| C.I-359 | A-8 | Cl | Cl | H | CH=CH—CH=CH | |
| C.I-360 | A-9 | Cl | Cl | H | CH=CH—CH=CH | |
| C.I-361 | A-1 | CF₃ | H | H | CH=CH—CH=CH | |
| C.I-362 | A-2 | CF₃ | H | H | CH=CH—CH=CH | |
| C.I-363 | A-3 | CF₃ | H | H | CH=CH—CH=CH | |
| C.I-364 | A-4 | CF₃ | H | H | CH=CH—CH=CH | |
| C.I-365 | A-5 | CF₃ | H | H | CH=CH—CH=CH | |
| C.I-366 | A-6 | CF₃ | H | H | CH=CH—CH=CH | |
| C.I-367 | A-7 | CF₃ | H | H | CH=CH—CH=CH | |
| C.I-368 | A-8 | CF₃ | H | H | CH=CH—CH=CH | |
| C.I-369 | A-9 | CF₃ | H | H | CH=CH—CH=CH | |

TABLE C.I.1-continued

| Compound I | A | R¹ | R² | R³ | R⁴ | R⁵ |
|---|---|---|---|---|---|---|
| C.I-370 | A-1 | $CF_3$ | Cl | H | CH=CH | CH=CH |
| C.I-371 | A-2 | $CF_3$ | Cl | H | CH=CH | CH=CH |
| C.I-372 | A-3 | $CF_3$ | Cl | H | CH=CH | CH=CH |
| C.I-373 | A-4 | $CF_3$ | Cl | H | CH=CH | CH=CH |
| C.I-374 | A-5 | $CF_3$ | Cl | H | CH=CH | CH=CH |
| C.I-375 | A-6 | $CF_3$ | Cl | H | CH=CH | CH=CH |
| C.I-376 | A-7 | $CF_3$ | Cl | H | CH=CH | CH=CH |
| C.I-377 | A-8 | $CF_3$ | Cl | H | CH=CH | CH=CH |
| C.I-378 | A-9 | $CF_3$ | Cl | H | CH=CH | CH=CH |
| C.I-379 | A-1 | H | H | Cl | CH=CH | CH=CH |
| C.I-380 | A-2 | H | H | Cl | CH=CH | CH=CH |
| C.I-381 | A-3 | H | H | Cl | CH=CH | CH=CH |
| C.I-382 | A-4 | H | H | Cl | CH=CH | CH=CH |
| C.I-383 | A-5 | H | H | Cl | CH=CH | CH=CH |
| C.I-384 | A-6 | H | H | Cl | CH=CH | CH=CH |
| C.I-385 | A-7 | H | H | Cl | CH=CH | CH=CH |
| C.I-386 | A-8 | H | H | Cl | CH=CH | CH=CH |
| C.I-387 | A-9 | H | H | Cl | CH=CH | CH=CH |
| C.I-388 | A-1 | H | Cl | Cl | CH=CH | CH=CH |
| C.I-389 | A-2 | H | Cl | Cl | CH=CH | CH=CH |
| C.I-390 | A-3 | H | Cl | Cl | CH=CH | CH=CH |
| C.I-391 | A-4 | H | Cl | Cl | CH=CH | CH=CH |
| C.I-392 | A-5 | H | Cl | Cl | CH=CH | CH=CH |
| C.I-393 | A-6 | H | Cl | Cl | CH=CH | CH=CH |
| C.I-394 | A-7 | H | Cl | Cl | CH=CH | CH=CH |
| C.I-395 | A-8 | H | Cl | Cl | CH=CH | CH=CH |
| C.I-396 | A-9 | H | Cl | Cl | CH=CH | CH=CH |
| C.I-397 | A-1 | Cl | H | Cl | CH=CH | CH=CH |
| C.I-398 | A-2 | Cl | H | Cl | CH=CH | CH=CH |
| C.I-399 | A-3 | Cl | H | Cl | CH=CH | CH=CH |
| C.I-400 | A-4 | Cl | H | Cl | CH=CH | CH=CH |
| C.I-401 | A-5 | Cl | H | Cl | CH=CH | CH=CH |
| C.I-402 | A-6 | Cl | H | Cl | CH=CH | CH=CH |
| C.I-403 | A-7 | Cl | H | Cl | CH=CH | CH=CH |
| C.I-404 | A-8 | Cl | H | Cl | CH=CH | CH=CH |
| C.I-405 | A-9 | Cl | H | Cl | CH=CH | CH=CH |
| C.I-406 | A-1 | Cl | Cl | Cl | CH=CH | CH=CH |
| C.I-407 | A-2 | Cl | Cl | Cl | CH=CH | CH=CH |
| C.I-408 | A-3 | Cl | Cl | Cl | CH=CH | CH=CH |
| C.I-409 | A-4 | Cl | Cl | Cl | CH=CH | CH=CH |
| C.I-410 | A-5 | Cl | Cl | Cl | CH=CH | CH=CH |
| C.I-411 | A-6 | Cl | Cl | Cl | CH=CH | CH=CH |
| C.I-412 | A-7 | Cl | Cl | Cl | CH=CH | CH=CH |
| C.I-413 | A-8 | Cl | Cl | Cl | CH=CH | CH=CH |
| C.I-414 | A-9 | Cl | Cl | Cl | CH=CH | CH=CH |
| C.I-415 | A-1 | $CF_3$ | H | Cl | CH=CH | CH=CH |
| C.I-416 | A-2 | $CF_3$ | H | Cl | CH=CH | CH=CH |
| C.I-417 | A-3 | $CF_3$ | H | Cl | CH=CH | CH=CH |
| C.I-418 | A-4 | $CF_3$ | H | Cl | CH=CH | CH=CH |
| C.I-419 | A-5 | $CF_3$ | H | Cl | CH=CH | CH=CH |
| C.I-420 | A-6 | $CF_3$ | H | Cl | CH=CH | CH=CH |
| C.I-421 | A-7 | $CF_3$ | H | Cl | CH=CH | CH=CH |
| C.I-422 | A-8 | $CF_3$ | H | Cl | CH=CH | CH=CH |
| C.I-423 | A-9 | $CF_3$ | H | Cl | CH=CH | CH=CH |
| C.I-424 | A-1 | $CF_3$ | Cl | Cl | CH=CH | CH=CH |
| C.I-425 | A-2 | $CF_3$ | Cl | Cl | CH=CH | CH=CH |
| C.I-426 | A-3 | $CF_3$ | Cl | Cl | CH=CH | CH=CH |
| C.I-427 | A-4 | $CF_3$ | Cl | Cl | CH=CH | CH=CH |
| C.I-428 | A-5 | $CF_3$ | Cl | Cl | CH=CH | CH=CH |
| C.I-429 | A-6 | $CF_3$ | Cl | Cl | CH=CH | CH=CH |
| C.I-430 | A-7 | $CF_3$ | Cl | Cl | CH=CH | CH=CH |
| C.I-431 | A-8 | $CF_3$ | Cl | Cl | CH=CH | CH=CH |
| C.I-432 | A-9 | $CF_3$ | Cl | Cl | CH=CH | CH=CH |
| C.I-433 | A-1 | H | H | $CF_3$ | CH=CH | CH=CH |
| C.I-434 | A-2 | H | H | $CF_3$ | CH=CH | CH=CH |
| C.I-435 | A-3 | H | H | $CF_3$ | CH=CH | CH=CH |
| C.I-436 | A-4 | H | H | $CF_3$ | CH=CH | CH=CH |
| C.I-437 | A-5 | H | H | $CF_3$ | CH=CH | CH=CH |
| C.I-438 | A-6 | H | H | $CF_3$ | CH=CH | CH=CH |
| C.I-439 | A-7 | H | H | $CF_3$ | CH=CH | CH=CH |
| C.I-440 | A-8 | H | H | $CF_3$ | CH=CH | CH=CH |
| C.I-441 | A-9 | H | H | $CF_3$ | CH=CH | CH=CH |
| C.I-442 | A-1 | H | Cl | $CF_3$ | CH=CH | CH=CH |
| C.I-443 | A-2 | H | Cl | $CF_3$ | CH=CH | CH=CH |
| C.I-444 | A-3 | H | Cl | $CF_3$ | CH=CH | CH=CH |
| C.I-445 | A-4 | H | Cl | $CF_3$ | CH=CH | CH=CH |
| C.I-446 | A-5 | H | Cl | $CF_3$ | CH=CH | CH=CH |
| C.I-447 | A-6 | H | Cl | $CF_3$ | CH=CH | CH=CH |
| C.I-448 | A-7 | H | Cl | $CF_3$ | CH=CH | CH=CH |
| C.I-449 | A-8 | H | Cl | $CF_3$ | CH=CH | CH=CH |
| C.I-450 | A-9 | H | Cl | $CF_3$ | CH=CH | CH=CH |
| C.I-451 | A-1 | Cl | H | $CF_3$ | CH=CH | CH=CH |
| C.I-452 | A-2 | Cl | H | $CF_3$ | CH=CH | CH=CH |
| C.I-453 | A-3 | Cl | H | $CF_3$ | CH=CH | CH=CH |
| C.I-454 | A-4 | Cl | H | $CF_3$ | CH=CH | CH=CH |
| C.I-455 | A-5 | Cl | H | $CF_3$ | CH=CH | CH=CH |
| C.I-456 | A-6 | Cl | H | $CF_3$ | CH=CH | CH=CH |
| C.I-457 | A-7 | Cl | H | $CF_3$ | CH=CH | CH=CH |
| C.I-458 | A-8 | Cl | H | $CF_3$ | CH=CH | CH=CH |
| C.I-459 | A-9 | Cl | H | $CF_3$ | CH=CH | CH=CH |
| C.I-460 | A-1 | Cl | Cl | $CF_3$ | CH=CH | CH=CH |
| C.I-461 | A-2 | Cl | Cl | $CF_3$ | CH=CH | CH=CH |
| C.I-462 | A-3 | Cl | Cl | $CF_3$ | CH=CH | CH=CH |
| C.I-463 | A-4 | Cl | Cl | $CF_3$ | CH=CH | CH=CH |
| C.I-464 | A-5 | Cl | Cl | $CF_3$ | CH=CH | CH=CH |
| C.I-465 | A-6 | Cl | Cl | $CF_3$ | CH=CH | CH=CH |
| C.I-466 | A-7 | Cl | Cl | $CF_3$ | CH=CH | CH=CH |
| C.I-467 | A-8 | Cl | Cl | $CF_3$ | CH=CH | CH=CH |
| C.I-468 | A-9 | Cl | Cl | $CF_3$ | CH=CH | CH=CH |
| C.I-469 | A-1 | $CF_3$ | H | $CF_3$ | CH=CH | CH=CH |
| C.I-470 | A-2 | $CF_3$ | H | $CF_3$ | CH=CH | CH=CH |
| C.I-471 | A-3 | $CF_3$ | H | $CF_3$ | CH=CH | CH=CH |
| C.I-472 | A-4 | $CF_3$ | H | $CF_3$ | CH=CH | CH=CH |
| C.I-473 | A-5 | $CF_3$ | H | $CF_3$ | CH=CH | CH=CH |
| C.I-474 | A-6 | $CF_3$ | H | $CF_3$ | CH=CH | CH=CH |
| C.I-475 | A-7 | $CF_3$ | H | $CF_3$ | CH=CH | CH=CH |
| C.I-476 | A-8 | $CF_3$ | H | $CF_3$ | CH=CH | CH=CH |
| C.I-477 | A-9 | $CF_3$ | H | $CF_3$ | CH=CH | CH=CH |
| C.I-478 | A-1 | $CF_3$ | Cl | $CF_3$ | CH=CH | CH=CH |
| C.I-479 | A-2 | $CF_3$ | Cl | $CF_3$ | CH=CH | CH=CH |
| C.I-480 | A-3 | $CF_3$ | Cl | $CF_3$ | CH=CH | CH=CH |
| C.I-481 | A-4 | $CF_3$ | Cl | $CF_3$ | CH=CH | CH=CH |
| C.I-482 | A-5 | $CF_3$ | Cl | $CF_3$ | CH=CH | CH=CH |
| C.I-483 | A-6 | $CF_3$ | Cl | $CF_3$ | CH=CH | CH=CH |
| C.I-484 | A-7 | $CF_3$ | Cl | $CF_3$ | CH=CH | CH=CH |
| C.I-485 | A-8 | $CF_3$ | Cl | $CF_3$ | CH=CH | CH=CH |
| C.I-486 | A-9 | $CF_3$ | Cl | $CF_3$ | CH=CH | CH=CH |

The examples of compounds I of formula I of table C.I.1 include their tautomers, racemic mixtures, individual pure enantiomers and diastereomers and their optically active mixtures.

General Preparation Methods of Compounds of Formula I

The active compounds I can be prepared according to methods as described in WO2005/085216, WO2007/074789 or in WO2007/079162.

Preferred Active Compounds II Selected from Group A

With respect to their use in the pesticidal mixtures of the present invention, particular preference is given to the compounds C.II as listed in the paragraphs below.

With regard to the use in a pesticidal mixture of the present invention, the compound II selected from group A.1 as defined above is preferably triazemate or primicarb.

With regard to the use in a pesticidal mixture of the present invention, the compound II selected from group A.2 as defined above is preferably endosulfan, N-Ethyl-2,2-dimethylpropionamide-2-(2,6-dichloro-α.α.α-trifluoro-p-tolyl)hydrazon, N-Ethyl-2,2-dichloro-1-methylcyclopropane-carboxamide-2-(2,6-dichloro-α.α.α-trifluoro-p-tolyl)hydrazon, acetoprole, ethiprole, fipronil, pyrafluprole, pyriprole or vaniliprole or the phenylpyrazole compound II.A$^{2.1}$.

More preferably the compound II is N-Ethyl-2,2-dimethylpropionamide-2-(2,6-dichloro-α.α.α-trifluoro-p-tolyl)hydrazon, N-Ethyl-2,2-dichloro-1-methylcyclopropane-carboxamide-2-(2,6-dichloro-α.α.α-trifluoro-p-tolyl)hydrazon, acetoprole or fipronil.

With regard to the use in a pesticidal mixture of the present invention, the compound II selected from group A.3 as defined above is preferably allethrin, bifenthrin, cyfluthrin, lambda-cyhalothrin, cypermethrin, alpha-cypermethrin, beta-cypermethrin, zeta-cypermethrin, deltamethrin, etofenprox, fenpropathrin, fenvalerate, flucythrinate, tau-fluvalinate, silafluofen or tralomethrin.

More preferably the compound II is alpha-cypermethrin or deltamethrin.

With regard to the use in a pesticidal mixture of the present invention, the compound II selected from group A.4 as defined above is preferably thiocyclam or from the class of neonicotinoids acteamiprid, chlothianidin, dinotefuran, imidacloprid, nitenpyram, thiacloprid, thiamethoxam and AKD-1022; or the allosteric nicotinic acteylcholine receptor agonist spinosad.

More preferably the compound II is clothianidine, imidacloprid or thiamethoxam.

With regard to the use in a pesticidal mixture of the present invention, the compound II selected from group A.5 as defined above is preferably abamectin, emamectin benzoate, lepimectin or milbemectin.

More preferably the compound II is abamectin.

With regard to the use in a pesticidal mixture of the present invention, the compound II selected from group A.7 as defined above is preferably diafenthiuron.

With regard to the use in a pesticidal mixture of the present invention, the compound II selected from group A.8 as defined above is preferably buprofezin.

With regard to the use in a pesticidal mixture of the present invention, the compound II selected from group A.10 as defined above is preferably pyridaben or flufenerim.

With regard to the use in a pesticidal mixture of the present invention, the compound II selected from group A.11 as defined above is preferably indoxacarb or metaflumizone. More preferably the compound II is metaflumizone.

With regard to the use in a pesticidal mixture of the present invention, the compound II selected from group A.12 as defined above is preferably spirodiclofen, spiromesifen or spirotetramat.

More preferably the compound II is spiromesifen or spirotetramat.

With regard to the use in a pesticidal mixture of the present invention, the compound II selected from group A.13 as defined above is preferably amitraz, flonicamid, flubendiamine, pymetrozine, pyridalyl, pyrifluquinazon, chlorantraniliproler, the anthranil compound II.A$^{13.1}$ or the sulfoximine compounds II.A$^{13.2}$, II.A$^{13.3}$ or II.A$^{13.4}$.

More preferably the compound II is flonicamid, pymetrozine, pyrifluquinazon, chlorantraniliprole or the anthranil compound II.A$^{13.1}$.

Especially preferred are pesticidal mixtures containing N-Ethyl-2,2-dimethylpropionamide-2-(2,6-dichloro-α.α.α-trifluoro-p-tolyl)hydrazon as compound II.

Especially preferred are pesticidal mixtures containing N-Ethyl-2,2-dichloro-1-methylcyclopropane-carboxamide-2-(2,6-dichloro-α.α.α-trifluoro-p-tolyl)hydrazon as compound II.

Especially preferred are pesticidal mixtures containing acetoprole as compound II.

Especially preferred are pesticidal mixtures containing fipronil as compound II.

Especially preferred are pesticidal mixtures containing alpha-cypermethrin as compound II.

Especially preferred are pesticidal mixtures containing clothianidin as compound II.

Especially preferred are pesticidal mixtures containing imidacloprid as compound II.

Especially preferred are pesticidal mixtures containing thiamethoxam as compound II.

Especially preferred are pesticidal mixtures containing pymetrozine as compound II.

Especially preferred are pesticidal mixtures containing flonicamid as compound II.

Especially preferred are pesticidal mixtures containing spiromesifen as compound II.

Especially preferred are pesticidal mixtures containing spirotetramat as compound II.

Especially preferred are pesticidal mixtures containing pyrifluquinazon as compound II.

Especially preferred are pesticidal mixtures containing chlorantraniliprole as compound II.

Especially preferred are pesticidal mixtures containing the anthranilamid compound II.A$^{13.1}$ (II.A$^{13.1}$)

as compound II.

Especially preferred are pesticidal mixtures containing the sulfoximine compound II.A$^{13.2}$.

(II.A$^{13.2}$)

as compound II.

Especially preferred are pesticidal mixtures containing the sulfoximine compound II.A$^{13.3}$ (II.A$^{13.3}$)

as compound II.

Especially preferred are pesticidal mixtures containing the sulfoximine compound IIA$^{13.4}$ (II.A$^{13.4}$)

as compound II.

Preferred Mixtures According to the Invention

Especially preferred are inventive mixtures wherein the compound II of group A is acetoprol and the compound I of formula I is a compound of Table C.I.1.

Especially preferred are inventive mixtures wherein the compound II of group A is fipronil and the compound I of formula I is a compound of Table C.I.1.

Especially preferred are inventive mixtures wherein the compound II of group A is N-Ethyl-2,2-dimethylpropionamide-2-(2,6-dichloro-α.α.α-trifluoro-p-tolyl)hydrazon and the compound I of formula I is a compound of Table C.I.1.

Especially preferred are inventive mixtures wherein the compound II of group A is N-Ethyl-2,2-dichloro-1-methyl-cyclopropane-carboxamide-2-(2,6-dichloro-α.α.α-trifluoro-p-tolyl)hydrazon and the compound I of formula I is a compound of Table C.I.1.

Especially preferred are inventive mixtures wherein the compound II of group A is alpha-cypermethrin and the compound I of formula I is a compound of Table C.I.1.

Especially preferred are inventive mixtures wherein the compound II of group A is deltamethrin and the compound I of formula I is a compound of Table C.I.1.

Especially preferred are inventive mixtures wherein the compound II of group A is clothianidin and the compound I of formula I is a compound of Table C.I.1.

Especially preferred are inventive mixtures wherein the compound II of group A is imidacloprid and the compound I of formula I is a compound of Table C.I.1.

Especially preferred are inventive mixtures wherein the compound II of group A is thiamethoxam and the compound I of formula I is a compound of Table C.I.1.

Especially preferred are inventive mixtures wherein the compound II of group A is abamectin and the compound I of formula I is a compound of Table C.I.1.

Especially preferred are inventive mixtures wherein the compound II of group A is pymetrozine and the compound I of formula I is a compound of Table C.I.1.

Especially preferred are inventive mixtures wherein the compound II of group A is flonicamid and the compound I of formula I is a compound of Table C.I.1.

Especially preferred are inventive mixtures wherein the compound II of group A is diafenthiuron and the compound I of formula I is a compound of Table C.I.1.

Especially preferred are inventive mixtures wherein the compound II of group A is buprofezin and the compound I of formula I is a compound of Table C.I.1.

Especially preferred are inventive mixtures wherein the compound II of group A is pyridaben and the compound I of formula I is a compound of Table C.I.1.

Especially preferred are inventive mixtures wherein the compound II of group A is flufenerim and the compound I of formula I is a compound of Table C.I.1.

Especially preferred are inventive mixtures wherein the compound II of group A is metaflumizone and the compound I of formula I is a compound of Table C.I.1.

Especially preferred are inventive mixtures wherein the compound II of group A is spiromesifen and the compound I of formula I is a compound of Table C.I.1.

Especially preferred are inventive mixtures wherein the compound II of group A is spirotetramat and the compound I of formula I is a compound of Table C.I.1.

Especially preferred are inventive mixtures wherein the compound II of group A is pyrifluquinazon and the compound I of formula I is a compound of Table C.I.1.

Especially preferred are inventive mixtures wherein the compound II of group A is chlorantraniliprole and the compound I of formula I is a compound of Table C.I.1.

Especially preferred are inventive mixtures wherein the compound II of group A is the anthranilamid compound II.A$^{13.1}$ and the compound I of formula I is a compound of Table C.I.1.

Especially preferred are inventive mixtures wherein the compound II of group A is the sulfoximine compound II.A$^{13.2}$ and the compound I of formula I is a compound of Table C.I.1.

Especially preferred are inventive mixtures wherein the compound II of group A is the sulfoximine compound II.A$^{13.3}$ and the compound I of formula I is a compound of Table C.I.1.

Especially preferred are inventive mixtures wherein the compound II of group A is the sulfoximine compound II.A$^{13.4}$ and the compound I of formula I is a compound of Table C.I.1.

The following table M represents preferred combinations of the active compounds I of formula I as defined in table C.I.1 and the active compounds II of group A in mixtures according to the invention:

TABLE M

| Mixture | Compound I | Compound-II | Mixture | Compound I | Compound II |
| --- | --- | --- | --- | --- | --- |
| M.1 | C.I-37 | acetoprole | M.221 | C.I-37 | diafenthiuron |
| M.2 | C.I-40 | acetoprole | M.222 | C.I-40 | diafenthiuron |
| M.3 | C.I-73 | acetoprole | M.223 | C.I-73 | diafenthiuron |
| M.4 | C.I-76 | acetoprole | M.224 | C.I-76 | diafenthiuron |
| M.5 | C.I-145 | acetoprole | M.225 | C.I-145 | diafenthiuron |
| M.6 | C.I-148 | acetoprole | M.226 | C.I-148 | diafenthiuron |
| M.7 | C.I-199 | acetoprole | M.227 | C.I-199 | diafenthiuron |
| M.8 | C.I-202 | acetoprole | M.228 | C.I-202 | diafenthiuron |
| M.9 | C.I-235 | acetoprole | M.229 | C.I-235 | diafenthiuron |
| M.10 | C.I-238 | acetoprole | M.230 | C.I-238 | diafenthiuron |
| M.11 | C.I-240 | acetoprole | M.231 | C.I-240 | diafenthiuron |
| M.12 | C.I-244 | acetoprole | M.232 | C.I-244 | diafenthiuron |
| M.13 | C.I-247 | acetoprole | M.233 | C.I-247 | diafenthiuron |
| M.14 | C.I-307 | acetoprole | M.234 | C.I-307 | diafenthiuron |
| M.15 | C.I-310 | acetoprole | M.235 | C.I-310 | diafenthiuron |
| M.16 | C.I-361 | acetoprole | M.236 | C.I-361 | diafenthiuron |
| M.17 | C.I-364 | acetoprole | M.237 | C.I-364 | diafenthiuron |
| M.18 | C.I-397 | acetoprole | M.238 | C.I-397 | diafenthiuron |
| M.19 | C.I-400 | acetoprole | M.239 | C.I-400 | diafenthiuron |
| M.20 | C.I-406 | acetoprole | M.240 | C.I-406 | diafenthiuron |
| M.21 | C.I-409 | acetoprole | M.241 | C.I-409 | diafenthiuron |
| M.22 | C.I-469 | acetoprole | M.242 | C.I-469 | diafenthiuron |
| M.23 | C.I-472 | acetoprole | M.243 | C.I-472 | diafenthiuron |
| M.24 | C.I-37 | fipronil | M.244 | C.I-37 | buprofezin |
| M.25 | C.I-40 | fipronil | M.245 | C.I-40 | buprofezin |

TABLE M-continued

| Mixture | Compound I | Compound-II | Mixture | Compound I | Compound II |
|---|---|---|---|---|---|
| M.26 | C.I-73 | fipronil | M.246 | C.I-73 | buprofezin |
| M.27 | C.I-76 | fipronil | M.247 | C.I-76 | buprofezin |
| M.28 | C.I-145 | fipronil | M.248 | C.I-145 | buprofezin |
| M.29 | C.I-148 | fipronil | M.249 | C.I-148 | buprofezin |
| M.30 | C.I-199 | fipronil | M.250 | C.I-199 | buprofezin |
| M.31 | C.I-202 | fipronil | M.251 | C.I-202 | buprofezin |
| M.32 | C.I-235 | fipronil | M.252 | C.I-235 | buprofezin |
| M.33 | C.I-238 | fipronil | M.253 | C.I-238 | buprofezin |
| M.34 | C.I.240 | fipronil | M.254 | C.I.240 | buprofezin |
| M.35 | C.I-244 | fipronil | M.255 | C.I-244 | buprofezin |
| M.36 | C.I-247 | fipronil | M.256 | C.I-247 | buprofezin |
| M.37 | C.I-307 | fipronil | M.257 | C.I-307 | buprofezin |
| M.38 | C.I-310 | fipronil | M.258 | C.I-310 | buprofezin |
| M.39 | C.I-361 | fipronil | M.259 | C.I-361 | buprofezin |
| M.40 | C.I-364 | fipronil | M.260 | C.I-364 | buprofezin |
| M.41 | C.I-397 | fipronil | M.261 | C.I-397 | buprofezin |
| M.42 | C.I-400 | fipronil | M.262 | C.I-400 | buprofezin |
| M.43 | C.I-406 | fipronil | M.263 | C.I-406 | buprofezin |
| M.44 | C.I-409 | fipronil | M.264 | C.I-409 | buprofezin |
| M.45 | C.I-469 | fipronil | M.265 | C.I-469 | buprofezin |
| M.46 | C.I-472 | fipronil | M.266 | C.I-472 | buprofezin |
| M.47 | C.I-37 | imidacloprid | M.267 | C.I-37 | pyridaben |
| M.48 | C.I-40 | imidacloprid | M.268 | C.I-40 | pyridaben |
| M.49 | C.I-73 | imidacloprid | M.269 | C.I-73 | pyridaben |
| M.50 | C.I-76 | imidacloprid | M.270 | C.I-76 | pyridaben |
| M.51 | C.I-145 | imidacloprid | M.271 | C.I-145 | pyridaben |
| M.52 | C.I-148 | imidacloprid | M.272 | C.I-148 | pyridaben |
| M.53 | C.I-199 | imidacloprid | M.273 | C.I-199 | pyridaben |
| M.54 | C.I-202 | imidacloprid | M.274 | C.I-202 | pyridaben |
| M.55 | C.I-235 | imidacloprid | M.275 | C.I-235 | pyridaben |
| M.56 | C.I-238 | imidacloprid | M.276 | C.I-238 | pyridaben |
| M.57 | C.I.240 | imidacloprid | M.277 | C.I.240 | pyridaben |
| M.58 | C.I-244 | imidacloprid | M.278 | C.I-244 | pyridaben |
| M.59 | C.I-247 | imidacloprid | M.279 | C.I-247 | pyridaben |
| M.60 | C.I-307 | imidacloprid | M.280 | C.I-307 | pyridaben |
| M.61 | C.I-310 | imidacloprid | M.281 | C.I-310 | pyridaben |
| M.62 | C.I-361 | imidacloprid | M.282 | C.I-361 | pyridaben |
| M.63 | C.I-364 | imidacloprid | M.283 | C.I-364 | pyridaben |
| M.64 | C.I-397 | imidacloprid | M.284 | C.I-397 | pyridaben |
| M.65 | C.I-400 | imidacloprid | M.285 | C.I-400 | pyridaben |
| M.66 | C.I-406 | imidacloprid | M.286 | C.I-406 | pyridaben |
| M.67 | C.I-409 | imidacloprid | M.287 | C.I-409 | pyridaben |
| M.68 | C.I-469 | imidacloprid | M.288 | C.I-469 | pyridaben |
| M.69 | C.I-472 | imidacloprid | M.289 | C.I-472 | pyridaben |
| M.70 | C.I-37 | abamectin | M.290 | C.I-37 | spiromesifen |
| M.71 | C.I-40 | abamectin | M.291 | C.I-40 | spiromesifen |
| M.72 | C.I-73 | abamectin | M.292 | C.I-73 | spiromesifen |
| M.73 | C.I-76 | abamectin | M.293 | C.I-76 | spiromesifen |
| M.74 | C.I-145 | abamectin | M.294 | C.I-145 | spiromesifen |
| M.75 | C.I-148 | abamectin | M.295 | C.I-148 | spiromesifen |
| M.76 | C.I-199 | abamectin | M.296 | C.I-199 | spiromesifen |
| M.77 | C.I-202 | abamectin | M.297 | C.I-202 | spiromesifen |
| M.78 | C.I-235 | abamectin | M.298 | C.I-235 | spiromesifen |
| M.79 | C.I-238 | abamectin | M.299 | C.I-238 | spiromesifen |
| M.80 | C.I.240 | abamectin | M.300 | C.I.240 | spiromesifen |
| M.81 | C.I-244 | abamectin | M.301 | C.I-244 | spiromesifen |
| M.82 | C.I-247 | abamectin | M.302 | C.I-247 | spiromesifen |
| M.83 | C.I-307 | abamectin | M.303 | C.I-307 | spiromesifen |
| M.84 | C.I-310 | abamectin | M.304 | C.I-310 | spiromesifen |
| M.85 | C.I-361 | abamectin | M.305 | C.I-361 | spiromesifen |
| M.86 | C.I-364 | abamectin | M.306 | C.I-364 | spiromesifen |
| M.87 | C.I-397 | abamectin | M.307 | C.I-397 | spiromesifen |
| M.88 | C.I-400 | abamectin | M.308 | C.I-400 | spiromesifen |
| M.89 | C.I-406 | abamectin | M.309 | C.I-406 | spiromesifen |
| M.90 | C.I-409 | abamectin | M.310 | C.I-409 | spiromesifen |
| M.91 | C.I-469 | abamectin | M.311 | C.I-469 | spiromesifen |
| M.92 | C.I-472 | abamectin | M.312 | C.I-472 | spiromesifen |
| M.93 | C.I-37 | anthranilamid II.A[13.1] | M.313 | C.I-37 | chlorantraniliprole |
| M.94 | C.I-40 | anthranilamid II.A[13.1] | M.314 | C.I-40 | chlorantraniliprole |
| M.95 | C.I-73 | anthranilamid II.A[13.1] | M.315 | C.I-73 | chlorantraniliprole |
| M.96 | C.I-76 | anthranilamid II.A[13.1] | M.316 | C.I-76 | chlorantraniliprole |
| M.97 | C.I-145 | anthranilamid II.A[13.1] | M.317 | C.I-145 | chlorantraniliprole |
| M.98 | C.I-148 | anthranilamid II.A[13.1] | M.318 | C.I-148 | chlorantraniliprole |

TABLE M-continued

| Mixture | Compound I | Compound-II | Mixture | Compound I | Compound II |
|---|---|---|---|---|---|
| M.99 | C.I-199 | anthranilamid II.A[13.1] | M.319 | C.I-199 | chlorantraniliprole |
| M.100 | C.I-202 | anthranilamid II.A[13.1] | M.320 | C.I-202 | chlorantraniliprole |
| M.101 | C.I-235 | anthranilamid II.A[13.1] | M.321 | C.I-235 | chlorantraniliprole |
| M.102 | C.I-238 | anthranilamid II.A[13.1] | M.322 | C.I-238 | chlorantraniliprole |
| M.103 | C.I.240 | anthranilamid II.A[13.1] | M.323 | C.I.240 | chlorantraniliprole |
| M.104 | C.I-244 | anthranilamid II.A[13.1] | M.324 | C.I-244 | chlorantraniliprole |
| M.105 | C.I-247 | anthranilamid II.A[13.1] | M.325 | C.I-247 | chlorantraniliprole |
| M.106 | C.I-307 | anthranilamid II.A[13.1] | M.326 | C.I-307 | chlorantraniliprole |
| M.107 | C.I-310 | anthranilamid II.A[13.1] | M.327 | C.I-310 | chlorantraniliprole |
| M.108 | C.I-361 | anthranilamid II.A[13.1] | M.328 | C.I-361 | chlorantraniliprole |
| M.109 | C.I-364 | anthranilamid II.A[13.1] | M.329 | C.I-364 | chlorantraniliprole |
| M.110 | C.I-397 | anthranilamid II.A[13.1] | M.330 | C.I-397 | chlorantraniliprole |
| M.111 | C.I-400 | anthranilamid II.A[13.1] | M.331 | C.I-400 | chlorantraniliprole |
| M.112 | C.I-406 | anthranilamid II.A[13.1] | M.332 | C.I-406 | chlorantraniliprole |
| M.113 | C.I-409 | anthranilamid II.A[13.1] | M.333 | C.I-409 | chlorantraniliprole |
| M.114 | C.I-469 | anthranilamid II.A[13.1] | M.334 | C.I-469 | chlorantraniliprole |
| M.115 | C.I-472 | anthranilamid II.A[13.1] | M.335 | C.I-472 | chlorantraniliprole |
| M.116 | C.I-37 | deltamethrin | M.336 | C.I-37 | flufenerim |
| M.117 | C.I-40 | deltamethrin | M.337 | C.I-40 | flufenerim |
| M.118 | C.I-73 | deltamethrin | M.338 | C.I-73 | flufenerim |
| M.119 | C.I-76 | deltamethrin | M.339 | C.I-76 | flufenerim |
| M.120 | C.I-145 | deltamethrin | M.340 | C.I-145 | flufenerim |
| M.121 | C.I-148 | deltamethrin | M.341 | C.I-148 | flufenerim |
| M.122 | C.I-199 | deltamethrin | M.342 | C.I-199 | flufenerim |
| M.123 | C.I-202 | deltamethrin | M.343 | C.I-202 | flufenerim |
| M.124 | C.I-235 | deltamethrin | M.344 | C.I-235 | flufenerim |
| M.125 | C.I-238 | deltamethrin | M.345 | C.I-238 | flufenerim |
| M.126 | C.I.240 | deltamethrin | M.346 | C.I.240 | flufenerim |
| M.127 | C.I-244 | deltamethrin | M.347 | C.I-244 | flufenerim |
| M.128 | C.I-247 | deltamethrin | M.348 | C.I-247 | flufenerim |
| M.129 | C.I-307 | deltamethrin | M.349 | C.I-307 | flufenerim |
| M.130 | C.I-310 | deltamethrin | M.350 | C.I-310 | flufenerim |
| M.131 | C.I-361 | deltamethrin | M.351 | C.I-361 | flufenerim |
| M.132 | C.I-364 | deltamethrin | M.352 | C.I-364 | flufenerim |
| M.133 | C.I-397 | deltamethrin | M.353 | C.I-397 | flufenerim |
| M.134 | C.I-400 | deltamethrin | M.354 | C.I-400 | flufenerim |
| M.135 | C.I-406 | deltamethrin | M.355 | C.I-406 | flufenerim |
| M.136 | C.I-409 | deltamethrin | M.356 | C.I-409 | flufenerim |
| M.137 | C.I-469 | deltamethrin | M.357 | C.I-469 | flufenerim |
| M.138 | C.I-472 | deltamethrin | M.358 | C.I-472 | flufenerim |
| M.139 | C.I-37 | metaflumizone | M.359 | C.I-37 | α-cypermethrin |
| M.140 | C.I-40 | metaflumizone | M.360 | C.I-40 | α-cypermethrin |
| M.141 | C.I-73 | metaflumizone | M.361 | C.I-73 | α-cypermethrin |
| M.142 | C.I-76 | metaflumizone | M.362 | C.I-76 | α-cypermethrin |
| M.143 | C.I-145 | metaflumizone | M.363 | C.I-145 | α-cypermethrin |
| M.144 | C.I-148 | metaflumizone | M.364 | C.I-148 | α-cypermethrin |
| M.145 | C.I-199 | metaflumizone | M.365 | C.I-199 | α-cypermethrin |
| M.146 | C.I-202 | metaflumizone | M.366 | C.I-202 | α-cypermethrin |
| M.147 | C.I-235 | metaflumizone | M.367 | C.I-235 | α-cypermethrin |
| M.148 | C.I-238 | metaflumizone | M.368 | C.I-238 | α-cypermethrin |
| M.149 | C.I.240 | metaflumizone | M.369 | C.I.240 | α-cypermethrin |
| M.150 | C.I-244 | metaflumizone | M.370 | C.I-244 | α-cypermethrin |
| M.151 | C.I-247 | metaflumizone | M.371 | C.I-247 | α-cypermethrin |
| M.152 | C.I-307 | metaflumizone | M.372 | C.I-307 | α-cypermethrin |
| M.153 | C.I-310 | metaflumizone | M.373 | C.I-310 | α-cypermethrin |
| M.154 | C.I-361 | metaflumizone | M.374 | C.I-361 | α-cypermethrin |
| M.155 | C.I-364 | metaflumizone | M.375 | C.I-364 | α-cypermethrin |
| M.156 | C.I-397 | metaflumizone | M.376 | C.I-397 | α-cypermethrin |
| M.157 | C.I-400 | metaflumizone | M.377 | C.I-400 | α-cypermethrin |
| M.158 | C.I-406 | metaflumizone | M.378 | C.I-406 | α-cypermethrin |
| M.159 | C.I-409 | metaflumizone | M.379 | C.I-409 | α-cypermethrin |

TABLE M-continued

| Mixture | Compound I | Compound-II | Mixture | Compound I | Compound II |
|---|---|---|---|---|---|
| M.160 | C.I-469 | metaflumizone | M.380 | C.I-469 | α-cypermethrin |
| M.161 | C.I-472 | metaflumizone | M.381 | C.I-472 | α-cypermethrin |
| M.162 | C.I-37 | clothianidine | M.382 | C.I-37 | thiamethoxam |
| M.163 | C.I-40 | clothianidine | M.383 | C.I-40 | thiamethoxam |
| M.164 | C.I-73 | clothianidine | M.384 | C.I-73 | thiamethoxam |
| M.165 | C.I-76 | clothianidine | M.385 | C.I-76 | thiamethoxam |
| M.166 | C.I-145 | clothianidine | M.386 | C.I-145 | thiamethoxam |
| M.167 | C.I-148 | clothianidine | M.387 | C.I-148 | thiamethoxam |
| M.168 | C.I-199 | clothianidine | M.388 | C.I-199 | thiamethoxam |
| M.169 | C.I-202 | clothianidine | M.389 | C.I-202 | thiamethoxam |
| M.170 | C.I-235 | clothianidine | M.390 | C.I-235 | thiamethoxam |
| M.171 | C.I-238 | clothianidine | M.391 | C.I-238 | thiamethoxam |
| M.172 | C.I.240 | clothianidine | M.392 | C.I.240 | thiamethoxam |
| M.173 | C.I-244 | clothianidine | M.393 | C.I-244 | thiamethoxam |
| M.174 | C.I-247 | clothianidine | M.394 | C.I-247 | thiamethoxam |
| M.175 | C.I-307 | clothianidine | M.395 | C.I-307 | thiamethoxam |
| M.176 | C.I-310 | clothianidine | M.396 | C.I-310 | thiamethoxam |
| M.177 | C.I-361 | clothianidine | M.397 | C.I-361 | thiamethoxam |
| M.178 | C.I-364 | clothianidine | M.398 | C.I-364 | thiamethoxam |
| M.179 | C.I-397 | clothianidine | M.399 | C.I-397 | thiamethoxam |
| M.180 | C.I-400 | clothianidine | M.400 | C.I-400 | thiamethoxam |
| M.181 | C.I-406 | clothianidine | M.401 | C.I-406 | thiamethoxam |
| M.182 | C.I-409 | clothianidine | M.402 | C.I-409 | thiamethoxam |
| M.183 | C.I-469 | clothianidine | M.403 | C.I-469 | thiamethoxam |
| M.184 | C.I-472 | clothianidine | M.404 | C.I-472 | thiamethoxam |
| M.185 | C.I-37 | flonicamid | M.405 | C.I-37 | spirotetramat |
| M.186 | C.I-40 | flonicamid | M.406 | C.I-40 | spirotetramat |
| M.187 | C.I-73 | flonicamid | M.407 | C.I-73 | spirotetramat |
| M.188 | C.I-76 | flonicamid | M.408 | C.I-76 | spirotetramat |
| M.189 | C.I-145 | flonicamid | M.409 | C.I-145 | spirotetramat |
| M.190 | C.I-148 | flonicamid | M.410 | C.I-148 | spirotetramat |
| M.191 | C.I-199 | flonicamid | M.411 | C.I-199 | spirotetramat |
| M.192 | C.I-202 | flonicamid | M.412 | C.I-202 | spirotetramat |
| M.193 | C.I-235 | flonicamid | M.413 | C.I-235 | spirotetramat |
| M.194 | C.I-238 | flonicamid | M.414 | C.I-238 | spirotetramat |
| M.195 | C.I.240 | flonicamid | M.415 | C.I.240 | spirotetramat |
| M.196 | C.I-244 | flonicamid | M.416 | C.I-244 | spirotetramat |
| M.197 | C.I-247 | flonicamid | M.417 | C.I-247 | spirotetramat |
| M.198 | C.I-307 | flonicamid | M.418 | C.I-307 | spirotetramat |
| M.199 | C.I-310 | flonicamid | M.419 | C.I-310 | spirotetramat |
| M.200 | C.I-361 | flonicamid | M.420 | C.I-361 | spirotetramat |
| M.201 | C.I-364 | flonicamid | M.421 | C.I-364 | spirotetramat |
| M.202 | C.I-397 | flonicamid | M.422 | C.I-397 | spirotetramat |
| M.203 | C.I-400 | flonicamid | M.423 | C.I-400 | spirotetramat |
| M.204 | C.I-406 | flonicamid | M.424 | C.I-406 | spirotetramat |
| M.205 | C.I-409 | flonicamid | M.425 | C.I-409 | spirotetramat |
| M.206 | C.I-469 | flonicamid | M.426 | C.I-469 | spirotetramat |
| M.207 | C.I-472 | flonicamid | M.427 | C.I-472 | spirotetramat |
| M.208 | C.I-37 | pymetrozine | M.428 | C.I-37 | pyrifluquinazone |
| M.209 | C.I-40 | pymetrozine | M.429 | C.I-40 | pyrifluquinazone |
| M.210 | C.I-73 | pymetrozine | M.430 | C.I-73 | pyrifluquinazone |
| M.211 | C.I-76 | pymetrozine | M.431 | C.I-76 | pyrifluquinazone |
| M.212 | C.I-145 | pymetrozine | M.432 | C.I-145 | pyrifluquinazone |
| M.213 | C.I-148 | pymetrozine | M.433 | C.I-148 | pyrifluquinazone |
| M.214 | C.I-199 | pymetrozine | M.434 | C.I-199 | pyrifluquinazone |
| M.215 | C.I-202 | pymetrozine | M.435 | C.I-202 | pyrifluquinazone |
| M.216 | C.I-235 | pymetrozine | M.436 | C.I-235 | pyrifluquinazone |
| M.217 | C.I-238 | pymetrozine | M.437 | C.I-238 | pyrifluquinazone |
| M.218 | C.I.240 | pymetrozine | M.438 | C.I.240 | pyrifluquinazone |
| M.219 | C.I-244 | pymetrozine | M.439 | C.I-244 | pyrifluquinazone |
| M.220 | C.I-247 | pymetrozine | M.440 | C.I-247 | pyrifluquinazone |
| M.221 | C.I-307 | pymetrozine | M.441 | C.I-307 | pyrifluquinazone |
| M.222 | C.I-310 | pymetrozine | M.442 | C.I-310 | pyrifluquinazone |
| M.223 | C.I-361 | pymetrozine | M.443 | C.I-361 | pyrifluquinazone |
| M.224 | C.I-364 | pymetrozine | M.444 | C.I-364 | pyrifluquinazone |
| M.225 | C.I-397 | pymetrozine | M.445 | C.I-397 | pyrifluquinazone |
| M.226 | C.I-400 | pymetrozine | M.446 | C.I-400 | pyrifluquinazone |
| M.227 | C.I-406 | pymetrozine | M.447 | C.I-406 | pyrifluquinazone |
| M.228 | C.I-409 | pymetrozine | M.448 | C.I-409 | pyrifluquinazone |
| M.229 | C.I-469 | pymetrozine | M.449 | C.I-469 | pyrifluquinazone |
| M.230 | C.I-472 | pymetrozine | M.450 | C.I-472 | pyrifluquinazone |

Pests

The mixtures of the active compounds I and II, or the active compounds I and II used simultaneously, that is jointly or separately, exhibit outstanding action against pests from the following orders:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctate, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula oleracea,* and *Tipula paludosa* thrips (Thysanoptera), e.g. *Dichromothrips corbetti, Dichromothrips* ssp, *Frankliniella fusca, Frankliniella occidentalis, Frankliniella tritici, Scirtothrips citri, Thrips oryzae, Thrips palmi* and *Thrips tabaci*, termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis*, true bugs (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Mazus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus*.

ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa*,

*Paravespula vulgaris, Paravespula pennsylvanica, Paravespula germanica, Dolichovespula maculata, Vespa crabro, Polistes rubiginosa, Camponotus floridanus,* and *Linepithema humile,* crickets, grasshoppers, locusts (Orthoptera), e.g. *Acheta domestics, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,*

Arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni*; Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus tetanus* and *Tetranychus urticae, Panonychus ulmi, Panonychus citri,* and *Oligonychus pratensis*; Araneida, e.g. *Latrodectus mactans,* and *Loxosceles reclusa,* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii,* and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species, ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species, sheath nematodes, *Hemicycliophora* species and *Hemicriconemoides* species; *Hirshmanniella* species; lance nematodes, *Hoplolaimus columbus, Hoplolaimus galeatus* and other *Hoplolaimus* species, false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species; *Radinaphelenchus cocophilus* and other *Radinaphelenchus* species, burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species, and other plant parasitic nematode species.

Moreover, the inventive mixtures are especially useful for the control of Lepidoptera, Coleoptera, Diptera, Thysanoptera and Hymenoptera.

In particular the inventive mixtures are useful for the control of Thysanoptera and Hymenoptera, especially Hymenoptera.

Formulations

The mixtures according to the present invention can be converted into the customary formulations, for example solutions, emulsions, suspensions, dusts, powders, pastes and granules. The use form depends on the particular intended purpose; in each case, it should ensure a fine and even distribution of the compounds according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP (N-methyl-pyrrolidone), NOP (N-octylpyrrolidone)), acetates (glycol diacetate), glycols, fatty acid dimethylamides, fatty acids and fatty acid esters. In principle, solvent mixtures may also be used.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

An example of a gelling agent is carrageen (Satiagel®)

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds. In this case, the active compounds are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compounds by weight, preferably 0.1 to 40% by weight.

The mixtures of the present invention can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:
1. Products for dilution with water for foliar applications. For seed treatment purposes, such products may be applied to the seed diluted or undiluted.
A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolve(s) upon dilution with water, whereby a formulation with 10% (w/w) of active compound(s) is obtained.
B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.
C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.
D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.
E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s).

J) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

Various types of oils, welters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

Applications

The compounds I and the one or more compound(s) II can be applied simultaneously, that is jointly or separately, or in succession, the sequence, in the case of separate application, generally not having any effect on the result of the control measures.

The mixtures of the invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The compounds I and the one or more compound(s) II are usually applied in a weight ratio of from 500:1 to 1:100, preferably from 20:1 to 1:50, in particular from 5:1 to 1:20. Depending on the desired effect, the application rates of the mixtures according to the invention are from 5 g/ha to 2000 g/ha, preferably from 50 to 1500 g/ha, in particular from 50 to 750 g/ha.

The mixtures according to the invention are effective through both contact and ingestion.

According to a preferred embodiment of the invention, the mixtures according to the present invention are employed via soil application. Soil application is especially favorable for use against ants, termites, crickets, or cockroaches.

According to another preferred embodiment of the invention, for use against non crop pests such as ants, termites, wasps, flies, mosquitoes, crickets, locusts, or cockroaches the mixtures according to the present invention are prepared into a bait preparation.

The bait can be a liquid, a solid or a semisolid preparation (e.g. a gel).

Another aspect of the present invention is when preparing the mixtures, it is preferred to employ the pure active compounds I and II, to which further active compounds, e.g. against harmful fungi or having herbicidal activity, or growth-regulating agents or fertilizers can be added.

Compositions of this invention may further contain other active ingredients than those listed above. For example fungicides, herbicides, fertilizers such as ammonium nitrate, urea, potash, and superphosphate, phytotoxicants and plant growth regulators and safeners. These additional ingredients may be used sequentially or in combination with the above-described compositions, if appropriate also added only immediately prior to use (tank mix). For example, the plant(s) may be sprayed with a composition of this invention either before or after being treated with other active ingredients.

The mixtures according to the invention can be applied to any and all developmental stages, such as egg, larva, pupa, and adult. The pests may be controlled by contacting the target pest, its food supply, habitat, breeding ground or its locus with a pesticidally effective amount of the inventive mixtures or of compositions comprising the mixtures.

"Locus" means a plant, seed, soil, area, material or environment in which a pest is growing or may grow.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally effective amount can vary for the various mixtures and/or compositions used in the invention. A pesticidally effective amount of the mixtures and/or compositions will also vary according to the prevailing conditions such as desired pesticidal effect and duration, weather, target species, locus, mode of application, and the like.

The inventive mixtures or compositions of these mixtures can also be employed for protecting plants from attack or infestation by insects, acarids or nematodes comprising contacting a plant, or soil or water in which the plant is growing.

The inventive mixtures are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non crop pests such as ants, termites, wasps, flies, mosquitoes, crickets, locusts, or cockroaches the inventive mixtures are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a composition including the inventive mixtures, optionally a repellent and at least one binder.

The inventive mixtures and the compositions comprising them can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient(s) ranges from 0.0001 to 500 g per 100 $m^2$, preferably from 0.001 to 20 g per 100 $m^2$.

Customary application rates in the protection of materials are, for example, from 0.01 g to 1000 g of active compound(s) per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient(s) is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the mixture of the active ingredients is from 0.001 to 80 weights %, preferably from 0.01 to 50 weight % and most preferably from 0.01 to 15 weight %.

For use in treating crop plants, the rate of application of the mixture of the active ingredients of this invention may be in the range of 0.1 g to 4000 g per hectare, desirably from 25 g to 600 g per hectare, more desirably from 50 g to 500 g per hectare.

In the context of the present invention, the term plant refers to an entire plant, a part of the plant or the plant propagation material.

The mixtures of the present invention and the compositions comprising them are particularly important in the control of a multitude of insects on various cultivated plants.

Plants which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be mentioned. These young plants may also be protected before transplantation by a total or partial treatment by immersion or pouring.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot be obtained by cross breeding, mutations or natural recombination. Typically, one or more genes have been integrated into the genetic material of a genetically modified plant in order to improve certain properties of the plant.

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see a g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins tolerance to harmful pests from all taxonomic groups of insects, especially to beetles (Coeloptera), two-winged insects (Diptera), and butterflies (Lepidoptera).

The term "cultivated plants" is to be understood also including plants that are by the use of recombinant DNA techniques capable to synthesize one or more proteins to in-crease the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

Some of the inventive mixtures have systemic action and can therefore be used for the protection of the plant shoot against foliar pests as well as for the treatment of the seed and roots against soil pests.

Seed Treatment

The mixtures according to the present invention are therefore suitable for the treatment of seeds in order to protect the seed from insect pest, in particular from soil-living insect pests and the resulting plant's roots and shoots against soil pests and foliar insects. The protection of the resulting plant's roots and shoots is preferred.

More preferred is the protection of resulting plant's shoots from piercing and sucking insects.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with mixtures according to the present invention. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound(s). The term "coated with and/or containing" generally signifies that the active ingredient(s) are for the most part on the surface of the propagation product at the time of application, although a greater or lesser part of the ingredient may penetrate into the propagation product, depending on the method of application. When the said propagation product are (re)planted, it may absorb the active ingredient.

Suitable seeds are seeds of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the mixtures according to the invention may also be used for the treatment seeds from plants, which tolerate the action of herbicides or fungicides or insecticides owing to breeding, including genetic engineering methods.

For example, the active mixtures can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the mixtures according to the present invention can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the mixtures is carried out by spraying or by dusting the seeds before sowing of the plants and before emergence of the plants.

In the treatment of seeds the corresponding formulations are applied by treating the seeds with an effective amount of the mixture according to the present invention. Herein, the application rates of the active compound(s) are generally from 0.1 g to 10 kg per 100 kg of seed, preferably from 1 g to 5 kg per 100 kg of seed, in particular from 1 g to 2.5 kg per 100 kg of seed. For specific crops such as lettuce the rate can be higher.

Compositions, which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient(s), 1-200 g/l Surfactant, 0 to 200 g/l antifreezing agent, 0 to 400 g/l of binder, 0 to 200 g/l of a pigment and up to 1 liter of a solvent, preferably water.

Preferred FS formulations of compounds of formula I for seed treatment usually comprise from 0.1 to 80% by weight (1 to 800 g/l) of the active ingredient(s), from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethanes, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The invention also relates to seed comprising mixtures according to the present invention. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed.

Animal Health

The mixtures of the present invention are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of mixture of the present invention or a composition comprising it.

The invention also provides a process for the preparation of a composition for treating, controlling, preventing or protecting animals against infestation or infection by parasites which comprises a parasiticidally effective amount of a mixture of the present invention or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that mixtures of the present invention are suitable for combating endo- and ectoparasites in and on animals.

Mixtures of the present invention and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Mixtures of the present invention and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The mixtures of the present invention and compositions comprising them are suitable for systemic and/or non-systemic control of ecto- and/or endoparasites. They are active against all or some stages of development.

The mixtures of the present invention are especially useful for combating ectoparasites.

The mixture of the present invention are especially useful for combating parasites of the following orders and species, respectively:

fleas (Siphonaptera), e.g. *Ctenocephalides fells, Ctenocephalides canis, Xenopsylla cheopis, Pulex irritans, Tunga penetrans*, and *Nosopsyllus fasciatus*, cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humans capitis, Pediculus humans corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*, Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The mixtures of the present invention and compositions containing them are particularly useful for the control of pests from the orders Diptera, Siphonaptera and Ixodida.

Moreover, the use of mixtures of the present invention and compositions containing them for combating mosquitoes is especially preferred.

The use of mixtures of the present invention and compositions containing them for combating flies is a further preferred embodiment of the present invention.

Furthermore, the use of the mixtures of the present invention and compositions containing them for combating fleas is especially preferred.

The use of the mixtures of the present invention and compositions containing them for combating ticks is a further preferred embodiment of the present invention.

The mixtures of the present invention also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the mixtures of the present invention may be formulated as animal feeds, animal feed premixes, animal feed concentrates, pills, solutions, pastes, suspensions, drenches, gels, tablets, boluses and capsules. In addition, the mixtures of the present invention may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the mixtures of the present invention may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the mixtures of the present invention may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the active compounds.

The mixtures of the present invention may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the active compounds. In addition, the active compound mixtures may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butyl hydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95 wt % of the active compounds of the mixtures of the present invention.

Generally it is favorable to apply the active compounds of the mixtures of the present invention in total amounts of 0.5 mg/kg to 100 mg/kg per day, preferably 1 mg/kg to 50 mg/kg per day.

Ready-to-use preparations contain the active compounds of the mixtures of the present invention acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the active compounds of the mixtures of the present invention acting against ectoparasites in concentrations of 0.5 to 90 percent by weight, preferably of 1 to 50 percent by weight.

Furthermore, the preparations comprise the active compounds of the mixtures of the present invention against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the mixtures of the present invention are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release the active compounds of the mixtures of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

EXAMPLES

Some of the preferred compound I examples are characterized by their physical data in the following table C.I.2. The characterization can be done by coupled High Performance Liquid Chromatography/mass spectrometry (HPLC/MS), by NMR or by their melting points.

The compounds were characterized by $^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: M=multiplett, q=quartett, t=triplett, d=doublet and s=singulett.

The compounds were also characterized by HPLC/MS. Analytical HPLC column: RP-18 column Chromolith Speed ROD from Merck KgaA, Germany). Elution: acetonitrile+ 0.1% trifluoroacetic acid (TFA)/water+0.1% trifluoroacetic acid (TFA) in a ratio of from 5:95 to 95:5 in 5 minutes at 40° C.

Physical data of some specific compound examples of isoxazoline compounds of formula I:

TABLE C.I.2

| Compound example | Structure of compound I | HPLC-MS ($t_r$ = retention time) | $^1$H NMR (in CDCl$_3$): δ [ppm] |
|---|---|---|---|
| C.I. 73 | | $t_r$ = 3.32 min; m = 494.0 | $^1$H-NMR (500 MHz, CDCl$_3$): δ = 8.50 (d, 1H), 7.95 (m, 1H), 7.90 (m, 2H), 7.70 (m, 3H), 7.52 (s, 2H), 7.40 (m, 1H), 7.35 (m, 1H), 7.25 (m, 1H), 4.75 (s, 2H), 4.10 (d, 1H), 3.75 (m, 1H). |
| C.I. 235 | | $t_r$ = 3.40 min; m = 508.0 | $^1$H-NMR (500 MHz, CDCl$_3$): δ = 8.55 (m, 1H), 7.70 (m, 1H), 7.50 (m, 5H), 7.45 (s, 1H), 7.40 (m, 1H), 7.25 (m, 2H), 4.75 (d, 2H), 4.05 (d, 1H), 3.68 (d, 1H), 2.50 (s, 3H). |
| C.I. 240 | | $t_r$ = 3.911 min; m = 556.1 | $^1$H-NMR (500 MHz, CDCl$_3$): δ = 7.42-7.58 (m, 6H), 7.01 (br dd, 1H), 6.77 (br. dd, 1H), 4.20 (d, 2H), 4.08 (d, 1H), 3.95 (m, 1H), 3.71 (d, 1H), 2.44 (s, 3H). |

TABLE C.I.2-continued

| Compound example | Structure of compound I | HPLC-MS ($t_r$ = retention time) | $^1$H NMR (in CDCl$_3$): δ [ppm] |
|---|---|---|---|
| C.I. 397 | | $t_r$ = 3.59 min; m = 544.1 | $^1$H-NMR (500 MHz, CDCl$_3$): δ = 8.85 (m, 1H), 8.52 (m, 1H), 8.47 (m, 1H), 7.30-7.80 (m, 10H), 7.25 (m, 1H), 4.85 (m, 2H), 4.26 (d, 1H), 3.88 (d, 1H). |

Biology

Synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, Weeds, 15, 20-22):

$$E = \frac{XY}{100}$$

When the observed combined control effect is greater than the expected combined control effect (E), then the combined effect is synergistic.

The following tests can demonstrate the control efficacy of compounds, mixtures or compositions of this invention on specific pests. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests.

Test B.1 Control of Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds or mixtures were formulated using a solution containing 75 wt % water and 25 wt % DMSO. Different concentrations of formulated compounds or mixtures were pipetted into the aphid diet, using a custom built pipetter, at two replications.

For experimental mixtures in these tests identical volumes of both mixing partners at the desired concentrations respectively, were mixed together.

After application, 5-8 adult aphids were placed on the artificial membrane inside the microtiter plate wells. The aphids were then allowed to suck on the treated aphid diet and incubated at 23±1° C., 50±5% RH for 3 days. Aphid mortality and fecundity was then visually assessed. For the mixture tested the results are listed in table B.1.

TABLE B.1

Control of Green Peach Aphid (*Myzus persicae*)

Test compound is C.I. 240:

| Green Peach Aphid | ppm | Average Control % |
|---|---|---|
| Thiamethoxam + test compound C.I. 240 | 0 + 2 | 0 |
| | 0.4 + 0 | 25 |
| | 0.4 + 2 | 100* |
| Imidacloprid + test compound C.I. 240 | 0 + 0.08 | 0 |
| | 0.4 + 0 | 0 |
| | 0.4 + 0.08 | 100* |

*synergistic control effect according to Colby's equation

Test B.2 Control of Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds or mixtures were formulated using a solution containing 75 wt % water and 25 wt % DMSO. Different concentrations of formulated compounds or mixtures were sprayed onto the insect diet at 20 µl, using a custom built micro atomizer, at two replications.

For experimental mixtures in these tests identical volumes of both mixing partners at the desired concentrations respectively, were mixed together.

After application, microtiter plates were incubated at 23±1° C., 50±5% RH for 5 days. Egg and larval mortality was then visually assessed. For the mixture tested the results are listed in table B.2.

TABLE B.2

Control of Boll Weevil (*Anthonomus grandis*)

Test compound is C.I. 240:

| Boll Weevil | ppm | Average Control % |
|---|---|---|
| Alpha-Cypermethrin + test compound C.I. 240 | 0 + 0.4 | 50 |
| | 0.08 + 0 | 0 |
| | 0.08 + 0.4 | 100* |
| Abamectin + test compound C.I. 240 | 0 + 0.08 | 0 |
| | 0.016 + 0 | 50 |
| | 0.016 + 0.08 | 100* |
| Flonicamid + test compound C.I.240 | 0 + 0.4 | 50 |
| | 4 + 0 | 0 |
| | 4 + 0.4 | 100* |

*synergistic control effect according to Colby's equation

In the following further test descriptions are given, which might also be used in order to evaluate the biological activity of the mixtures of the invention.

Test B.3

For evaluating control of vetch aphid (*Megoura viciae*) through contact or systemic means the test unit consists of 24-well-microtiter plates containing broad bean leaf disks.

The compounds or mixtures are formulated using a solution containing 75 wt % water and 25 wt % DMSO. Different concentrations of formulated compounds or mixtures are sprayed onto the leaf disks at 2.5 μl, using a custom built micro atomizer, at two replications.

For experimental mixtures in these tests identical volumes of both mixing partners at the desired concentrations respectively, are mixed together.

After application, the leaf disks are air-dried and 5-8 adult aphids are placed on the leaf disks inside the microtiter plate wells. The aphids are then allowed to suck on the treated leaf disks and incubated at 23±1° C., 50±5% RH (relative humidity) for 5 days. Aphid mortality and fecundity is then visually assessed.

Test B.4

For evaluating control of Mediterranean fruitfly (*Ceratitis capitata*) the test unit consists of 96-well-microtiter plates containing an insect diet and 50-80 *C. capitata* eggs.

The compounds or mixtures are formulated using a solution containing 75 wt % water and 25 wt % DMSO. Different concentrations of formulated compounds or mixtures are sprayed onto the insect diet at 5 μl, using a custom built micro atomizer, at two replications.

For experimental mixtures in these tests identical volumes of both mixing partners at the desired concentrations respectively, are mixed together.

After application, microtiter plates are incubated at 28±1° C., 80±5% RH for 5 days. Egg and larval mortality is visually assessed.

Test B.5

For evaluating control of tobacco budworm (*Heliothis virescens*) the test unit consists of 96-well-microtiter plates containing an insect diet and 15-25 *H. virescens* eggs.

The compounds or mixtures are formulated using a solution containing 75 wt % water and 25 wt % DMSO. Different concentrations of formulated compounds or mixtures are sprayed onto the insect diet at 10 μl, using a custom built micro atomizer, at two replications.

For experimental mixtures in these tests identical volumes of both mixing partners at the desired concentrations respectively, are mixed together.

After application, microtiter plates are incubated at 28±1° C., 80±5% RH for 5 days. Egg and larval mortality is visually assessed.

Test B.6

For evaluating control of bird cherry aphid (*Rhopalosiphum padi*) through contact or systemic means the test unit consists of 96-well-microtiter plates containing barley leaf disks.

The compounds or mixtures are formulated using a solution containing 75 wt % water and 25 wt % DMSO. Different concentrations of formulated compounds or mixtures are sprayed onto the leaf disks at 2.5 μl, using a custom built micro atomizer, at two replications.

For experimental mixtures in these tests identical volumes of both mixing partners at the desired concentrations respectively, are mixed together.

After application, the leaf disks are air-dried and 5-8 adult aphids placed on the leaf disks inside the microtiter plate wells. The aphids are then allowed to suck on the treated leaf disks and incubated at 25±1° C., 80±5% RH for 3 to 5 days. Aphid mortality and fecundity is visually assessed.

The invention claimed is:

1. A pesticial mixture comprising
1) at least one isoxazoline compound I of formula I:

wherein
A is and wherein # denotes the bond in formula I
$R^1$, $R^3$ are independently from one another selected from the group consisting of hydrogen, chloro or $CF_3$;
$R^2$ is hydrogen or chloro;
$R^4$ is hydrogen or $CH_3$, $R^5$ is hydrogen, or $R^4$ and $R^5$ are together a bridging 1,3-butadienyl group, which form—together with the aromatic phenylring C they are attached to—a naphtyl ring;

or the tautomers, enantiomers, diastereomers or salts thereof, and 2) at least one active compound II selected from group A consisting of A.2 a GABA-gated chloride channel antagonist selected from the class of phenylpyrazoles consisting of acetoprole, ethiprole, fipronil, pyrafluprole, pyriprole, vaniliprole and the phenylpyrazole compound II.A$^{2.1}$:

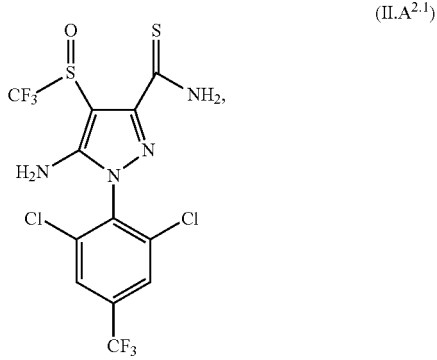 [SMILES: NC(=S)c1nn(-c2c(Cl)cc(C(F)(F)F)cc2Cl)c(N)c1S(=O)C(F)(F)F]

(II.A$^{2.1}$)

in synergistically effective amounts, wherein the active compound I of formula I and the active compound II are present in a weight ratio of from 500:1 to 1:100.

2. The mixture according to claim 1, wherein the substituents of the active compound I of formula I have the following meanings:

$R^1$, $R^2$, $R^3$ are chloro;
$R^4$ is hydrogen or CH$_3$,
$R^5$ is hydrogen or
$R^4$ and $R^5$ are together a bridging 1,3-butadienyl group, which form—together with the aromatic phenylring C they are attached to—a naphtyl ring;
or the tautomers, enantiomers, diastereomers or salts thereof.

3. The mixture according to claim 1, wherein the substituents of the active compound I of formula I have the following meanings:

$R^1$, $R^3$ are chloro;
$R^2$ is hydrogen;
$R^4$ is hydrogen or CH$_3$,
$R^5$ is hydrogen or
$R^4$ and $R^5$ are together a bridging 1,3-butadienyl group, which form—together with the aromatic phenylring C they are attached to—a naphtyl ring;
or the tautomers, enantiomers, diastereomers or salts thereof.

4. The mixture according to claim 1, wherein the substituents of the active compound I of formula I have the following meanings:

$R^1$, $R^3$ are CF$_3$;
$R^2$ is hydrogen;
$R^4$ is hydrogen or CH$_3$,
$R^5$ is hydrogen or
$R^4$ and $R^5$ are together a bridging 1,3-butadienyl group, which form—together with the aromatic phenylring C they are attached to—a naphtyl ring;
or the tautomers, enantiomers, diastereomers or salts thereof.

5. The mixture according to claim 1, wherein the substituents of the active compound I of formula I have the following meanings:

$R^1$ is CF$_3$;
$R^2$, $R^3$ are hydrogen;
$R^4$ is hydrogen or CH$_3$,
$R^5$ is hydrogen or
$R^4$ and $R^5$ are together a bridging 1,3-butadienyl group, which form—together with the aromatic phenylring C they are attached to—a naphtyl ring;
or the tautomers, enantiomers, diastereomers or salts thereof.

6. The mixture according to claim 1, wherein at least one active compound II is fipronil.

7. A method for protecting plants from attack or infestation by insects, acarids or nematodes comprising contacting the plant, or the soil or water in which the plant is growing, with a mixture according to claim 1 in pesticidally effective amounts.

8. A method for controlling insects, arachnids or nematodes comprising contacting an insect, acarid or nematode or their food supply, habitat, breeding grounds or their locus with a mixture according to claim 1 in pesticidally effective amounts.

9. A method as claimed in claim 8, wherein the mixture according claim 1 is applied in an amount of from 5 g/ha to 2000 g/ha.

10. A method for protection of plant propagation material comprising contacting the plant propagation material with a mixture of claim 1 in pesticidally effective amounts.

11. A method according to claim 10 wherein the mixture is applied in an amount of from 0.1 g to 10 kg per 100 kg of plant propagation material.

12. A method as claimed in claim 10, wherein the plant propagation material is/are seed(s).

13. A seed treated with the mixture according to claim 1 in an amount of from 0.1 g to 10 kg per 100 kg of seeds.

14. A method for protecting animals against infestation or infection by parasites which comprises administering to the animals a parasitically effective amount of a mixture according to claim 1 to the animal in need thereof.

15. A method for treating animals infested or infected by parasites which comprises administering to the animals a parasitically effective amount of a mixture according claim 1 to the animal in need thereof.

16. A method as claimed in claim 7 wherein the active compounds I of formula I and the active compounds II are applied simultaneously, that is jointly or separately, or in succession.

17. A pesticidal or parasiticidal composition, comprising a liquid or solid carrier and a mixture according to claim 1.

* * * * *

UNITED STATES PATENT AND TRADEMARK OFFICE
CERTIFICATE OF CORRECTION

PATENT NO. : 8,563,474 B2  
APPLICATION NO. : 13/003037  
DATED : October 22, 2013  
INVENTOR(S) : Karsten Koerber et al.

Page 1 of 1

It is certified that error appears in the above-identified patent and that said Letters Patent is hereby corrected as shown below:

In the Claims:

In Claim 1, col. 50, line 35, delete "pesticial" and insert therefore --pesticidal--; and line 65, delete "or" and insert therefore --and--.

Signed and Sealed this  
Thirteenth Day of May, 2014

Michelle K. Lee  
*Deputy Director of the United States Patent and Trademark Office*